US012318425B2

(12) United States Patent
Ranka et al.

(10) Patent No.: US 12,318,425 B2
(45) Date of Patent: Jun. 3, 2025

(54) FORMULATION COMPRISING WATER SOLUBLE PARTICLES OF A NON-CURCUMINOID AND A CURCUMINOID

(71) Applicants: STABICON LIFE SCIENCES PVT. LTD., Bangalore (IN); LYRUS LIFE SCIENCES PVT. LTD., Bangalore (IN); NOKHA TRADING LLP, Bangalore (IN)

(72) Inventors: Vijay Kumar Ranka, Bangalore (IN); Malini Sharma, Bangalore (IN); Pranab Kumar Patra, Bangalore (IN); Gulabusein Soudagar, Bangalore (IN); Yashvanth G, Bangalore (IN); Hemanth Kumar Bothra, Bangalore (IN); Shrinivasan Shesha Iyengar, Bangalore (IN)

(73) Assignees: Stabicon Life Sciences Pvt. Ltd., Bangalore (IN); Lyrus Life Sciences Pvt. Ltd., Bangalore (IN); Nokha Trading LLP, Bangalore (IN)

( * ) Notice: Subject to any disclaimer, the term of this patent is extended or adjusted under 35 U.S.C. 154(b) by 918 days.

(21) Appl. No.: 17/280,385

(22) PCT Filed: Oct. 23, 2019

(86) PCT No.: PCT/IN2019/050780
§ 371 (c)(1),
(2) Date: Mar. 26, 2021

(87) PCT Pub. No.: WO2020/084634
PCT Pub. Date: Apr. 30, 2020

(65) Prior Publication Data
US 2022/0054580 A1 Feb. 24, 2022

(30) Foreign Application Priority Data
Oct. 23, 2018 (IN) .............. 201841039937

(51) Int. Cl.
*A61K 36/00* (2006.01)
*A61K 9/107* (2006.01)
*A61K 31/12* (2006.01)
*A61K 36/9066* (2006.01)
*A61K 47/38* (2006.01)

(52) U.S. Cl.
CPC ........ *A61K 36/9066* (2013.01); *A61K 9/1075* (2013.01); *A61K 31/12* (2013.01); *A61K 47/38* (2013.01)

(58) Field of Classification Search
None
See application file for complete search history.

(56) References Cited

U.S. PATENT DOCUMENTS

| 7,879,373 | B2 | 2/2011 | Antony |
| 8,568,815 | B2 | 10/2013 | Parkkinen |
| 8,835,509 | B2 | 9/2014 | Kohli et al. |
| 9,259,401 | B2 | 2/2016 | Deshpande et al. |
| 9,474,727 | B2 | 10/2016 | Khamar et al. |
| 2005/0084526 | A1 | 4/2005 | Alander et al. |
| 2008/0226755 | A1* | 9/2008 | Antony ............... A61P 25/28 424/725 |
| 2013/0005339 | A1 | 1/2013 | Iwamura |
| 2016/0128939 | A9 | 5/2016 | Behnam |

FOREIGN PATENT DOCUMENTS

| EP | 3035947 A1 | 6/2016 |
| WO | 2007103435 A2 | 9/2007 |
| WO | 2010010431 A1 | 1/2010 |
| WO | 2012024405 A2 | 2/2012 |
| WO | 2014111956 A1 | 7/2014 |

OTHER PUBLICATIONS

International Search Report and Written Opinion mailed on Jan. 10, 2020 for PCT Application No. PCT/IN2019/050780, 8 pages.
Anuchapreeda, S., et al., "Preparation of Lipid Nanoemulsions Incorporating Curcumin for Cancer Therapy," Journal of Nanotechnology, vol. 2012, Article ID 270383, Hindawi Publishing Corporation, pp. 1-12.
Kurita, T. and Makino, Y., "Novel Curcumin Oral Delivery Systems," Anticancer Research, vol. 33, No. 7, Jul. 2013, pp. 2807-2822.
Anand et al., "Bioavailability of Curcumin: Problems and Promises", Molecular Pharmaceutics, vol. 4, No. 6, Sep. 28, 2007, pp. 807-818, URL: https://pubs.acs.org/doi/abs/10.1021/mp700113r.
(Continued)

*Primary Examiner* — Russell G Fiebig
(74) *Attorney, Agent, or Firm* — Shumaker & Sieffert, P.A.

(57) ABSTRACT

Embodiments relate to a formulation comprising a particle comprising a turmeric oleoresin or a curcumin removed turmeric oleoresin or a turmeric oil or combination thereof wherein the composition is water-soluble and therapeutically safe, wherein the composition does not contain a pH buffer, and wherein the composition further comprises a curcuminoid.

10 Claims, 16 Drawing Sheets

(56) References Cited

OTHER PUBLICATIONS

Bagchi, "Extraction of curcumin", IOSR Journal of Environmental Science, Toxicology and Food Technology, vol. 1, No. 3, Sep. 2012, pp. 1-16, Retrieved from the Internet on Dec. 29, 2023 from URL: https://www.iosrjournals.org/iosr-jestft/papers/vol1-issue3/A0130116.pdf.

Begum et al., "Curcumin Structure-Function, Bioavailability, and Efficacy in Models of Neuroinflammation and Alzheimer's Disease", Journal of Pharmacology and Experimental Therapeutics, vol. 326, No. 1, Jul. 1, 2008, pp. 196-208.

Bisht et al., "Polymeric nanoparticle-encapsulated curcumin ("nanocurcumin"): a novel strategy for human cancer therapy", Journal of Nanobiotechnology, vol. 5, No. 3, Apr. 17, 2007, 18 pp., URL: https://jnanobiotechnology.biomedcentral.com/articles/10.1186/1477-3155-5-3.

Chattopadhyay et al., "Turmeric and curcumin: Biological actions and medicinal applications", Current Science, vol. 87, No. 1, Jul. 10, 2004, pp. 44-53, URL: http://repository.ias.ac.in/5196/1/306.pdf.

Exbrayat et al., "Harmful Effects of Nanoparticles on Animals", Journal of Nanotechnology, Hindawi Publishing Corporation, Nov. 3, 2015, 11 pp., URL: https://www.hindawi.com/journals/jnt/2015/861092/.

Ferreira et al., "(Un) suitability of the use of pH buffers in biological, biochemical and environmental studies and their interaction with metal ions-a review", Royal Society of Chemistry, vol. 5, No. 39, RSC Publishing, Mar. 13, 2015, pp. 30989-31003, URL: https://repositorium.sdum.uminho.pt/bitstream/1822/38712/1/document_19948_1.pdf.

Gera et al., "Nano compositions of curcumin: an emerging paradigm for improved remedial application", Oncotarget, vol. 8, No. 39, Jul. 11, 2017, pp. 66680-66698, URL: https://www.ncbi.nlm.nih.gov/pmc/articles/PMC5630447/pdf/oncotarget-08-66680.pdf.

Guddadarangavvanahally et al., "Chemical Composition of Turmeric Oil—A Byproduct from Turmeric Oleoresin Industry and Its Inhibitory Activity against Different Fungi", Zeitschrift für Naturforschung C, vol. 56, No. 1-2, Feb. 1, 2001, pp. 40-44, URL: https://www.degruyter.com/journal/key/znc/html?lang=de.

International Preliminary Report on Patentability from International Application No. PCT/IN2019/050780 dated Apr. 27, 2021, 6 pp.

Jayaprakasha et al., "Chemical composition of turmeric oil—A by product from turmeric oleoresin industry and its inhibitory activity against different fungi", Zeitschriftfur Naturforschung C, vol. 56, No. 1-2, Feb. 1, 2001, pp. 40-44, UEL: https://www.degruyter.com/document/doi/10.1515/znc-2001-1-207/html.

Khedekar et al., "Self Emulsifying Drug Delivery System: A Review", International Journal of Pharmaceutical Sciences and Research, vol. 4, No. 12, Dec. 1, 2013, pp. 4494-4507, URL: https://ijpsr.com/bft-article/self-emulsifying-drug-delivery-system-a-review/.

Kuttan et al., "Potential anticancer activity of turmeric (*Curcuma longa*)", Cancer Letters, vol. 29, No. 2, Elsevier Scientific Publishers Ireland Ltd., Sep. 12, 1985, pp. 197-202.

Modasiya et al., "Studies on solubility of curcumin", vol. 3, No. 3, Mar. 2012, 8 pp.

Nagarajan et al., "Separation of Curcuminoids Enriched Fraction from Spent Turmeric Oleoresin and Its Antioxidant Potential", Journal of food science, vol. 75, No. 6, John Wiley & Sons, Inc., Aug. 17, 2010, pp. H158-H162, URL: https://ift.onlinelibrary.wiley.com/doi/abs/10.1111/j.1750-3841.2010.01696.x.

Nair et al., "Non-Curcuminoids from Turmeric and Their Potential in Cancer Therapy and Anticancer Drug Delivery Formulations", Biomolecules, vol. 9, No. 1, MDPI, Jan. 2, 2019, 36 pp., URL: https://www.mdpi.com/2218-273X/9/1/13.

Pisano et al., "Enhanced anti-tumor activity of a new curcumin-related compound against melanoma and neuroblastoma cells", Molecular Cancer, vol. 9, No. 137, Jun. 3, 2010, 12 pp., URL: https://link.springer.com/content/pdf/10.1186/1476-4598-9-137.pdf.

Ravindranath et al., "Absorption and tissue distribution of curcumin in rats", Toxicology, vol. 16, No. 3, Elsevier, Jun. 27, 1980, pp. 259-265, URL: https://www.sciencedirect.com/science/article/abs/pii/0300483X80901225.

Shoba et al., "Influence of Piperine on the Pharmacokinetics of Curcumin in Animals and Human Volunteers", Planta medica, vol. 64, No. 4, May 1998, pp. 353-356, Retrieved from the Internet on Dec. 29, 2023 from URL: https://web.archive.org/web/20160331004435id_/http://turmericaustralia.com.au/wp-content/uploads/2015/06/Influence-of-Piperine-on-the-Pharmacokinetics-of-Curcumin-in-Animal-and-Human-Volunteers.pdf.

Subramani et al., "Nanostructures for Curcumin Delivery: Possibilities and Challenges", Nano-and Microscale Drug Delivery Systems, Elsevier Inc., Jan. 1, 2017, pp. 393-418, Chapter 21.

Sui et al., "Inhibition of the HIV-1 and HIV-2 proteases by curcumin and curcumin boron complexes", Bioorganic & Medicinal Chemistry, vol. 1, No. 6, Pergamon Press Ltd., Sep. 30, 1993, pp. 415-422.

Wadhwa et al., "Emulsion forming drug delivery system for lipophilic drugs", Polish Pharmaceutical Society, vol. 69, No. 2, Apr. 2012, pp. 179-191, Retrieved from the Internet on Dec. 29, 2023 from URL: https://citeseerx.ist.psu.edu/document?repid=rep1&type=pdf&doi=955e3f9e6412448d34465cc327e4f938c858794d.

* cited by examiner

Correlation Function

Correlation Function

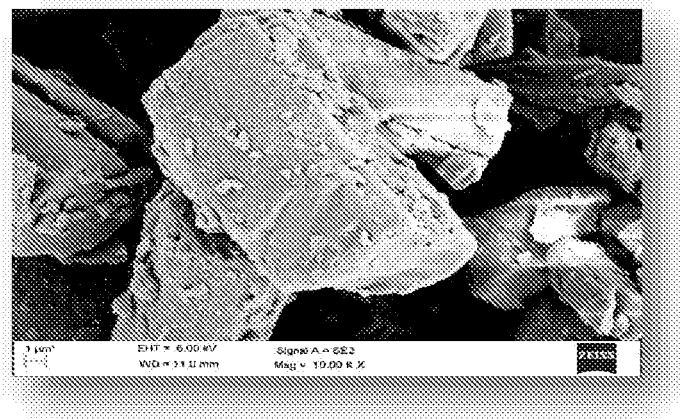
Fig. 6a (1)
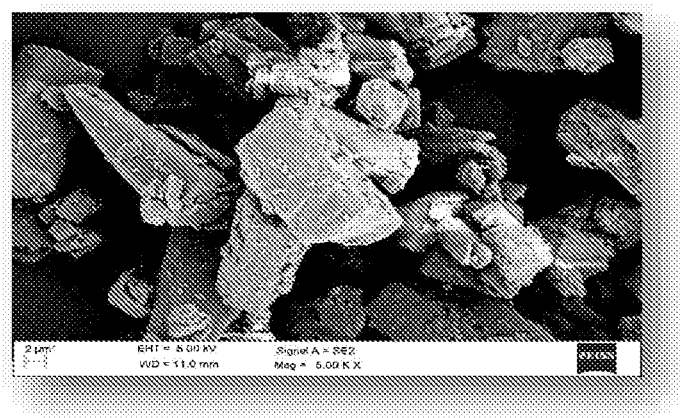
Fig. 6a (2)

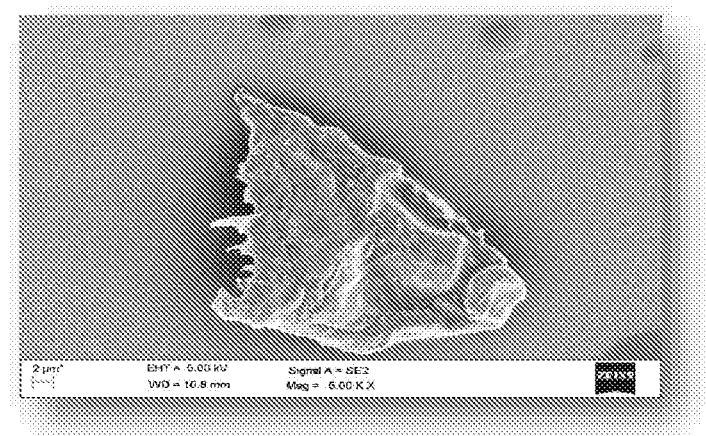
Fig. 6b
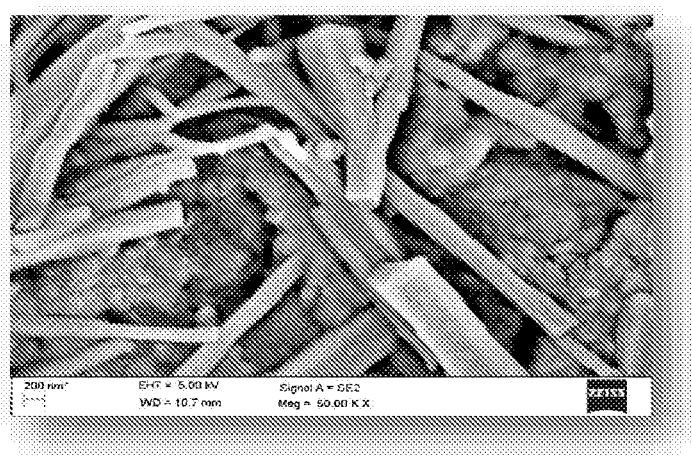
Fig. 6c (1)

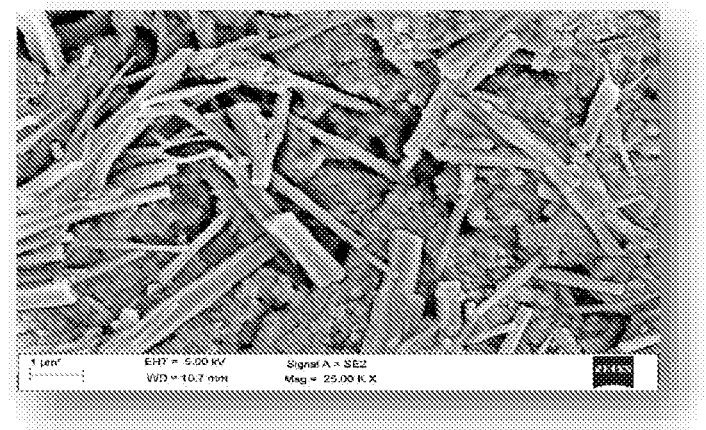
Fig. 6c (2)
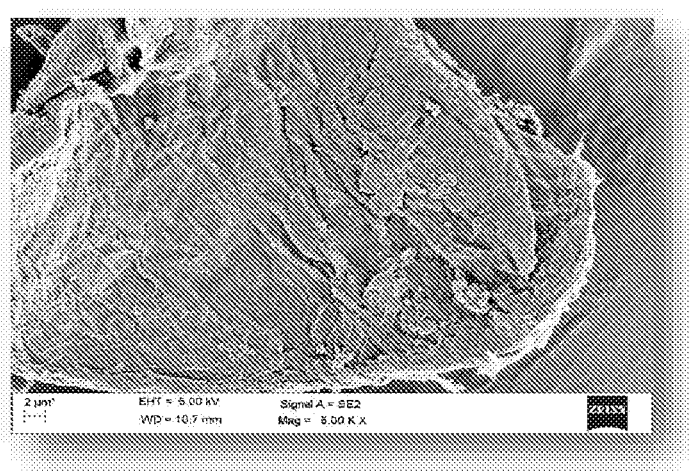
Fig. 6d (1)

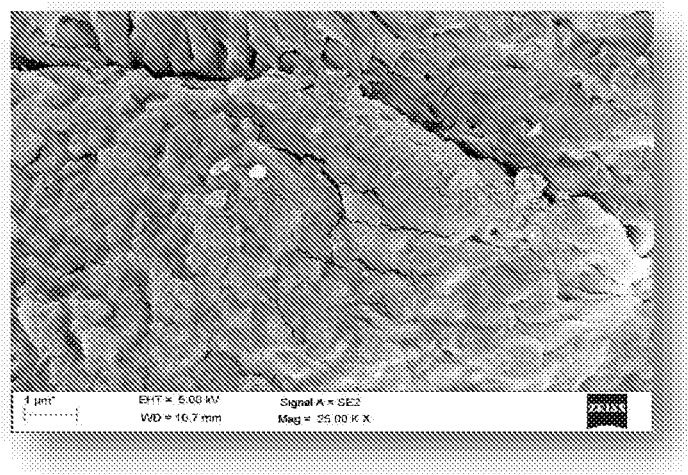
Fig. 6d (2)
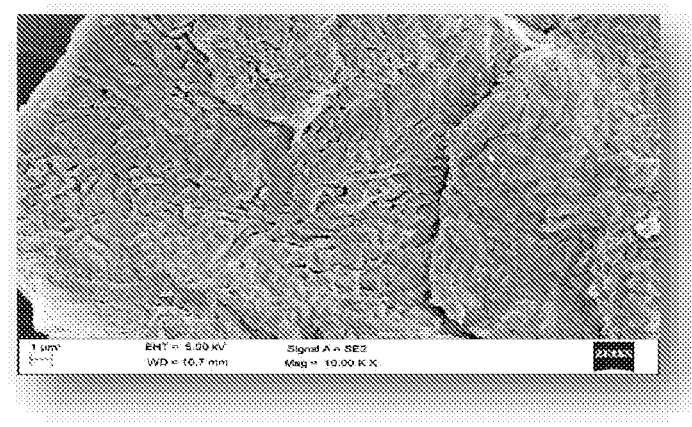
Fig. 6d (3)

Fig. 6d (4)

FORMULATION COMPRISING WATER SOLUBLE PARTICLES OF A NON-CURCUMINOID AND A CURCUMINOID

CROSS-REFERENCE TO RELATED APPLICATIONS

This application is the U.S. National Stage Entry of PCT/IN2019/050780, filed on Oct. 23, 2019, which claims priority to Indian Provisional Application No. IN 201841039937, entitled "CURCUMIN COMPOSITIONS AND PROCESS FOR PREPARING SAME" filed on Oct. 23, 2018, which are incorporated herein by reference in its entirety.

FIELD OF THE INVENTION

The present invention relates to the field of cosmetics, pharmaceuticals, nutraceuticals, and food products. The present invention further relates to the water-soluble compositions of curcuminoids and non-curcuminoids and formulations thereof.

BACKGROUND OF INVENTION

The background information on turmeric is disclosed in many prior arts: 'The turmeric (*Curcuma longa*) plant is a perennial herb cultivated extensively in south and southeast tropical Asia'. The rhizome of this plant is the most useful part of the plant for culinary and medicinal purposes. 'Turmeric rhizomes are processed to obtain turmeric powder initially, which on solvent extraction gives turmeric oleoresin (TO)' (Nagarajan et al., 2010). TO are rich in curcuminoids and non-curcuminoids (non-curcuminoids are biologically active curcumin-free compounds derived from Turmeric). Curcuminoids are the yellow color pigments of turmeric and are isolated from the turmeric oleoresin. Curcuminoids have been extensively studied for medicinal properties. Curcumin is the major type of curcuminoids. 'Curcumin has been shown to exhibit antioxidant, anti-inflammatory, antimicrobial, and anticarcinogenic activities. Additionally, the hepato- and nephro-protective, thrombosis suppressing, myocardial infarction protective, hypoglycemic, and antirheumatic effects of curcumin are also well established' (Anand P et al., 2007).

Jayaprakasha et al. (2001) state, 'The mother liquor after isolation of curcumin from oleoresin is known as curcumin removed turmeric oleoresin (CRTO).' CRTO is considered as an industrial waste at present and is being thrown into boilers. CRTO have shown antimicrobial properties (Jayaprakasha et al., 2001). CRTO are also natural antioxidant/preservative as well as colorant in various foods (Nagarajan et al., 2010). It has composition of non-curcuminoids comprising of oil and resin along with left over curcuminoids. 'Non-curcuminoids have a broad spectrum of anticancer activities on different cell lines including intricate and drug resistant malignancies.' 'Clinical studies were also conducted on these formulations based non-curcuminoids which consolidate promising results that make them strong contender in the medicinal market to fight numerous diseases especially cancer.' (Nair et al., 2019 review the beneficial effect of non-curcuminoids).

Curcuminoids (or curcumin) and non-curcuminoids health benefits and therapeutic uses have been limited due to low solubility and bioavailability (Nair et al., 2019; Anand P et al., 2007).

To date, 'To improve the bioavailability of curcumin, numerous approaches have been undertaken. These approaches involve, first, the use of adjuvant like piperine that interferes with glucuronidation; second, the use of liposomal curcumin; third, curcumin nanoparticles; fourth, the use of curcumin phospholipid complex; and fifth, the use of structural analogues of curcumin (e.g., EF-24)' (Anand P et al., 2007).

U.S. Pat. No. 8,568,815 B2 relates to 'A method of producing a water-soluble complex of curcumin with an alkyl or ether derivative of gamma-cyclodextrin comprising: a) curcumin with the gamma-cyclodextrin derivative at a molar ratio of about 1:1 to 1:6 in an aqueous phase at a pH of at least 11 to form a solution, and b) lowering the pH of the solution to below pH 8, whereby a stable cyclodextrin complex of curcumin is formed in said aqueous phase.' The prior art discloses use of pH buffers in the formulation. The use of pH in the therapeutic formulation may lead to unknown changes in ion-dependent biochemical reactions in biological system. Ferreira et al., 2015 states that 'Buffers such as phosphate, citrate, borate and succinate have some disadvantages when they are used in biological or complex systems.'

US 2016/0128939 A9 relates to 'A solubilisate composed of curcumin in a quantity of less than or equal to 10% by weight, preferably less than or equal to 7.5% by weight, particularly preferably 6% by weight, and at least one emulsifier having an HLB value in the range between 13 and 18, in particular polysorbate 80 or polysorbate 20 or a mixture of polysorbate 20 and polysorbate 80, wherein the average diameter of the micelles loaded with curcumin is between 5 nm and 40 nm, preferably between 6 nm and 20 nm, particularly preferably between 7 nm and 10 nm.' The small sized nanoparticles may lead to nanotoxicity and therefore, are potentially therapeutically unsafe. Exbrayat et al. (2015) states nanoparticles (NP) due to small size, 'migrate into the cell and reach organelles such as mitochondria, modifying the cell metabolism and provoking cell death. Exbrayat et al. also found that harmful toxicity of nanoparticles is more pronounced in smaller sized nanoparticles.'

As per our findings, we found that there has been no work on improving solubility and bioavailability of non-curcuminoids as defined above. Non-curcuminoids are 'also equally potent as curcuminoids' (Nair et al., 2019). A water-soluble formulation containing a curcuminoid and a non-curcuminoid that is both therapeutically safe and stable as a water-soluble formulation does not exist.

Therefore, there is an unmet and long-felt need to develop a water-soluble formulation comprising a curcuminoid and a non-curcuminoid, or pharmaceutically acceptable salts or derivatives thereof, wherein the water-soluble formulation is both therapeutically safe and stable in a form of the water-soluble formulation.

OBJECT OF INVENTION

An embodiment relates to a water-soluble curcuma formulation comprising a curcuminoid and a non-curcuminoid and an emulsifier without pH buffer.

Another embodiment relates to a water-soluble curcuma formulation comprising a curcuminoid and a non-curcuminoid with improved stability as a self-nanoemulsifying formulation.

Another embodiment relates to a water-soluble curcuma formulation comprising a curcuminoid and a non-curcuminoid with ultrafine to fine particles that are therapeutically safe.

An embodiment relates to a water-soluble curcuma formulation comprising Curcumin removed turmeric oleoresin—CRTO and a curcuminoid and emulsifier without pH buffer.

Another embodiment relates to a water-soluble curcuma comprising CRTO and a curcuminoid with improved stability as a self-nanoemulsifying formulation.

Another embodiment relates to a water-soluble curcuma formulation comprising CRTO and a curcuminoid with ultrafine to fine particles that are therapeutically safe.

Another embodiment relates to a water-soluble curcuma formulation comprising Turmeric oleoresin—TO and a curcuminoid and emulsifier without pH buffer.

Another embodiment relates to a water-soluble curcuma formulation comprising TO and a curcuminoid with improved biostability as a self-nanoemulsifying formulation.

Another embodiment relates to a water-soluble curcuma formulation comprising TO and a curcuminoid with ultrafine to fine particles that are therapeutically safe.

Another embodiment relates to a water-soluble curcuma formulation comprising Turmeric Oil—TOIL and a curcuminoid and emulsifier without pH buffer.

Another embodiment relates to a water-soluble curcuma formulation comprising TOIL and a curcuminoid with improved biostability as a self-nanoemulsifying formulation.

Another embodiment relates to a water-soluble composition comprising TOIL and a curcuminoid with ultrafine to fine particles that are therapeutically safe Another embodiment relates to a water-soluble curcuma formulation comprising TO or CRTO or TOIL or a combination thereof and a curcuminoid with ultrafine to fine particles that are therapeutically safe.

SUMMARY OF INVENTION

An embodiment relates to a curcuma formulation comprising a particle comprising a turmeric oleoresin or a curcumin removed turmeric oleoresin—CRTO wherein the composition is water soluble and therapeutically safe.

Other embodiments relate to a curcuma formulation wherein: the composition does not contain a pH buffer, and wherein the composition further comprises a curcuminoid; the composition comprises about 1 weight % to about 10 weight % of the curcuminoid; the composition comprises greater than about 10 weight % of the curcuminoid; the composition comprises about 40 to 70 weight % of the turmeric oleoresin; the turmeric oleoresin comprises of about 50 to 97% of the curcuminoid and 50-99% of a turmerone; the composition comprises about 5 to 69 wt % of the curcumin removed turmeric oleoresin; the curcumin removed turmeric oleoresin comprises about 1 to 50% of the curcuminoid and 50-99% of a turmerone; the composition further comprises a non-ionic oil-in-water emulsifier; the composition has HLB between 9 to 18 and more preferably between 11 and 16; the composition comprises about 30 to 45 weight % of the non-ionic oil-in-water emulsifier; the non-ionic oil-in-water emulsifier are selected from polyoxyethylene products of hydrogenated vegetable oils, polyethoxylated castor oils, polyethoxylated hydrogenated castor oil, polyoxyethylene-sorbitan-fatty acid esters, polyoxyethylene castor oil derivatives and/or a combination thereof, the composition further comprises a solvent; the solvent comprises ethyl alcohol, isopropyl alcohol, glycofurol, a polyethylene glycol, glycerol, a polypropylene glycol, a propylene glycol, N-methyl-2-pyrolidone or mixture thereof; the particle has size between 1000 to 40 nm; wherein the particle has a size preferably less than 500 nm.

Another embodiment relates to a curcuma formulation comprising a particle comprising a curcuminoid, a non-curcuminoid and a lipophilic solvent.

Other embodiments relate to the lipophilic solvent in the curcuma formulation is about 5 weight % to about 70 wt % of the composition; the lipophilic solvent in the composition is about 50 to about 200 weight % of the curcuminoid; the lipophilic solvent comprises a triglyceride; the triglyceride comprises a fractionated oil, a caprylic triglyceride, an oil containing chain fatty acid triglyceride, isopropyl myristate, isopropyl palmitate, ethyl linoleate, an ethyl oleate ester of fatty acid, propylene glycol dicaprylate, propylene glycol dilaurate or an oil containing propylene glycol fatty acid ester; the composition further comprises a non-ionic oil-in-water emulsifier; the composition comprises about 30 weight % to about 45 weight % of the non-ionic oil-in-water emulsifier; the non-ionic oil-in-water emulsifier comprises a polyoxyethylene product of a hydrogenated vegetable oil, a polyethoxylated castor oil, a polyethoxylated hydrogenated castor oil, a polyoxyethylene-sorbitan-fatty acid ester, a polyoxyethylene castor oil derivative or a combination thereof; the composition further comprises a solvent; the solvent comprises ethyl alcohol, isopropyl alcohol, glycofurol, a polyethylene glycol, glycerol, a polypropylene glycol, a propylene glycol, N-methyl-2-pyrolidone, ethyl alcohol or mixture thereof; the particle has size between 1000 to 40 nm; the particle has size preferably less than 500 nm; the composition further comprises a pharmaceutically acceptable excipient; the composition further comprises an adsorbent; the adsorbent comprises a polyethylene glycol, a maltodextrin, a soluble starch, a hydrolysed starch, a fiber, a water soluble oligo saccharide, a chicory, a dextran, a cellulose, a copolymer of polyvinylpyrrolidone, a sugar alcohol, a sorbitol, a xylitol, a mannitol, a cellulose derivative or combinations thereof; the cellulose derivative comprises a hydroxypropylmethyl cellulose, a hydroxypropyl cellulose, a cyclodextrine or combinations thereof, the composition further comprises a diluent, a filler or a binder; the diluent, the filler or the binder comprises a mannitol, a sorbitol, a lactose, a candy, a sugar or combinations thereof; the composition further comprises a water-soluble polymer; the water-soluble polymer comprises a polyglutamic acid, a polyethylene glycol, a propylene glycol, glycerol, a propylene glycol ester, a polyglycerol oleate polyvinyl alcohol, a non-ethoxylated polymer or combination thereof, the composition further comprises a stabilizer, a surfactant, a plasticizer, a lubricant, a reducing agent, a buffer agent, a sweetening agent, a base, an adsorbent, a corrigent, a binder, a suspending agent, an antioxidant, a polish, a coating, a wetting agent, a gelling agent, a wet modifier, a filler, an antifoaming agent, a refrigerative agent, a coloring matter, a flavoring agent, a perfume, a sugar coating agent, an isotonizing agent, a softener, an emulsifying agent, a foaming agent, a pH modifier, an anti-frothing agent, a flavouring agent, a preservative, a diluent, an excipient, a dispersing agent, a disintegrator, a fragrance, a desiccant, an antiseptic, a preservative, a solubilizing agent, a solubilizer, a solvent, a superplasticizer, an antistatic agent, an extender, a moisturizing agent, or combinations thereof, the composition is in a form comprising a solid form, a semisolid form or a liquid form; the form comprises a liquid drop, a powder, a tablet, a capsule, a lozenge, a transdermal patch, a cream or combination thereof; the tablet is orally soluble and dissolves in less than 15 to 30 minutes under a tongue or a buccal cavity of a human; the curcumin comprises a plurality of curcuminoids; the formulation could further comprise a pharmaceutical acceptable excipient; and wherein the formulation comprises a plurality of curcuminoids and a plurality of non-curcuminoids.

Another embodiment relates to a water-soluble curcuma formulation comprising a curcuminoid and a non-curcuminoid, or pharmaceutically acceptable salts or derivatives thereof, wherein the water-soluble formulation is both therapeutically safe and stable in a form of the water-soluble formulation.

Yet another embodiment relates to a water-soluble curcuma formulation comprising a first particle comprising a curcuminoid and a second particle comprising curcumin-removed turmeric oleoresin comprising a non-curcuminoid, or pharmaceutically acceptable salts or derivatives thereof, wherein the water-soluble formulation is both therapeutically safe and stable in a form of the water-soluble formulation.

Yet another embodiment relates to a water-soluble curcuma formulation comprising a first particle comprising a curcuminoid and a second particle comprising a non-curcuminoid derived from turmeric oleoresin or curcumin-removed turmeric oleoresin or turmeric oil or a combination thereof, or pharmaceutically acceptable salts or derivatives thereof, wherein the water-soluble formulation is both therapeutically safe and stable in a form of the water-soluble formulation.

Yet another embodiment relates to a formulation comprising a composition comprising a curcuminoid and a non-curcuminoid, wherein the composition has properties as follows: a) solubilization of the curcuminoid in a turmeric oleoresin or a curcumin removed turmeric oleoresin or a turmeric oil or combination thereof resulting in a clear solution having a percent sediment load of less than 30%; b) solubilization in the turmeric oleoresin or the curcumin removed turmeric oleoresin or the turmeric oil or combination of the curcuminoid and the non-curcuminoid having particles having an average number particle size in a range of 40 to 1000 nm; c) the formulation exhibits no precipitation or separation of the particles for a minimum period of 24 hours; d) the formulation exhibits no precipitation or separation of the particles for a minimum period of 15 minutes when added to water in a ratio of one part of the formulation in 200 parts of water.

Another embodiment relates to a method for preparation of water-soluble curcuma liquids comprising mixing a curcuminoid, a CRTO, a non-ionic oil in water emulsifier and a solvent to form a uniform blend; sonicating blend of step (a) for ten seconds at a time and resting for thirty seconds alternatingly to obtain clear solution; and diluting clear solution in aqueous medium to obtain desired concentration of curcuma liquid drops.

Another embodiment relates to a method for preparation of water-soluble curcuma powder comprising mixing a curcuminoid, a CRTO and a non-ionic emulsifier to form a uniform blend; sonicating the blend of step (a) for ten seconds at a time and resting for thirty seconds alternatingly to obtain a thick paste; adding an adsorbent under continuous stirring to obtain a mixture; cooling the mixture of step (c) obtaining a dry brittle mass; pulverizing the dry brittle mass obtaining a water-soluble curcuma powder; and packing the water-soluble curcuma powder.

Another embodiment relates to a method for preparation of transdermal curcuma patches.

Another embodiment relates to a method for preparation of water-soluble curcuma liquids comprising mixing a curcuminoid, a medium chain triglycerides, a non-ionic emulsifier, an adsorbent and a solvent to form a blend; sonicating the blend of step (a) for ten seconds at a time and resting for thirty seconds alternatingly, obtaining clear solution; and diluting clear solution in aqueous medium to obtain desired concentration of the curcuma liquid drops.

BRIEF DESCRIPTION OF THE FIGURES

FIG. 3c shows graphical correlation between the particle size and time taken for shift (Shift time or lag time) of TO.

FIG. 4c shows particle size distribution of TO.
FIG. 6a (1) shows SEM image of curcumin powder.
FIG. 6a (2) shows magnified SEM image of curcumin powder.
FIG. 6b shows SEM image of CRTO
FIG. 6c (1) shows SEM image of in-process blended mixed structure.
FIG. 6c (2) shows magnified SEM image of in-process blended mixed structure.
FIG. 6d (1) shows SEM image of intermediate blended solidified mixed structure.

FIG. 6d (2) shows SEM image of intermediate blended solidified mixed structure.

FIG. 6d (3) shows SEM image of intermediate blended solidified mixed structure.

FIG. 6d (4) shows SEM image of intermediate blended solidified mixed structure.

DETAILED DESCRIPTION

Figure 1:
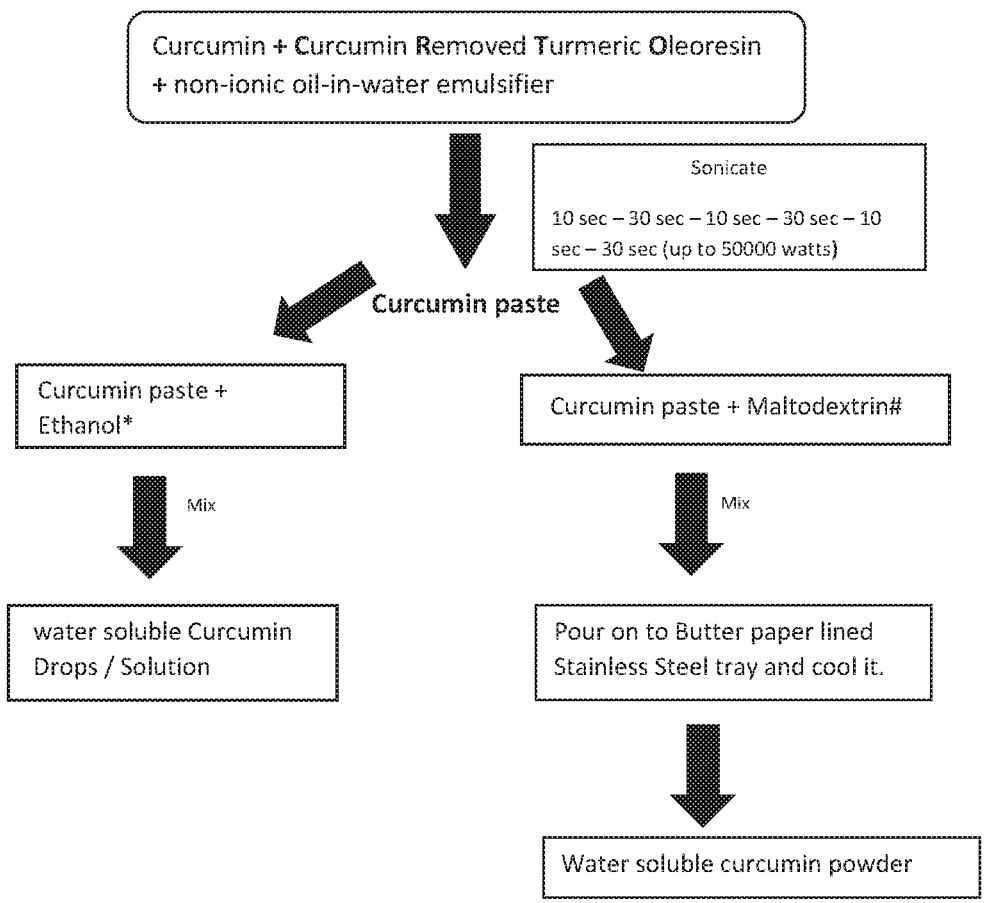
FIG. 1 shows flow diagram of curcuma formulation.

The articles "a" and "an" are used herein refers to one or to more than one (i.e., to at least one) of the grammatical object of the article. By way of example, "an element" means one element or more than one element.

The term "comprising", which is synonymous with "including", "containing", or "characterized by" here is defined as being inclusive or open-ended, and does not exclude additional, unrecited elements or method steps, unless the context clearly requires otherwise.

All percentages are defined as w/w unless stated otherwise. All measurements are defined according to International Standard of Units (SI) unless written otherwise.

In order to fully understand the scope of the invention, the following terms used herein are hereby defined.

The term "therapeutically safe" means enabling desired therapeutic efficacy through a formulation comprising combined key active components of Turmeric comprising a curcuminoid and a non-curcuminoid at lower doses, wherein the dose has a combined curcuminoid and non-curcuminoid content in the range of 1 mg to 500 mg.

The term "curcuma" is defined as a formulation having combination of the biologically active compounds of Turmeric comprising a curcuminoid and a non-curcuminoid.

The term "water-soluble" is defined as the ability of the curcuma liquid formulation to remain in clear solution form without precipitation or separation of the particles for a minimum period of 24 hours and the ability of curcuma formulation to result into a clear and transparent solution, without precipitation or separation of particles for a minimum period of 15 minutes when added to water in ratio of 1:200 and above.

The term Curcumin is defined as the principal biologically active curcuminoid found and derived from Turmeric.

The term Curcuminoid is defined as a linear diarylheptanoid found and derived from Turmeric, comprising curcumin or derivatives of curcumin.

The terms "curcumin", "curcuminoid" and "curcuminoids" may be used interchangeably unless otherwise stated differently. The native curcumin may comprise curcumin, demethoxycurcumin, bisdemethoxycurcumin and/or mixtures thereof.

The term "non-curcuminoid" is defined as a biologically active compound other than a curcuminoid, more particularly a curcumin-free bioactive compound found and derived from Turmeric.

The term Turmeric is defined as rhizomatous herbaceous perennial plant of the Curcuma species of the ginger family, Zingiberaceae, more particularly Curcuma *Longa,*

The term "pH buffer" is defined as a mixture of a weak acid and its conjugate base or a weak base and its conjugate acid.

The term "pharmaceutically acceptable excipient" is defined as substances other than the active pharmaceutical ingredient (API) that have been appropriately evaluated for safety and are intentionally included in a drug delivery system which facilitate processing of the drug formulation during its manufacture; protect, support, and/or enhance stability, bioavailability, or patient acceptability; facilitate in the effectiveness and/or delivery of the drug formulation and assist in maintaining the integrity of the drug formulation during its storage across its shelf life.

The term "particle" is defined as a minute portion of a substance which when having a size range between 1 and 100 nanometers are called as ultrafine and/or nano particles and having size range between 100 and 2500 nanometers are termed as fine particles.

The term Effective diameter is defined as the average size of particles in a given sample, wherein the effective diameter is equal to the total diameter of particles in the given sample divided by the number of particles in the given sample.

The term Polydispersity is a measure of the width of a particle size and is denoted by Polydispersity Index—PDI. PDI is a representation of the distribution of particle size populations within a given sample wherein the numerical value of PDI ranges from 0.0 for a perfectly uniform sample with respect to the particle size to 1.0 for a highly polydisperse sample with multiple particle size populations.

The term percent sediment load of less than 30% is defined as undistinguishable haziness in a clear solution caused by particles in the solution when viewed through naked eye. and is measured by calculating the residue left over on a Whatmann filter paper number 42 post filtering the clear solution through the filter paper.

The term "stable" is defined as the curcuma formulation when stored at normal ambient conditions (Temperature 25° C. and Relative Humidity 60%) for a period of up to 6 months, when added to water in ratio of 1:200 and above, results in a clear and transparent solution, without separation or precipitation of the particles for a minimum period of 15 minutes within which period the solution prepared from addition of curcuma formulation to water is orally consumed.

The term, "turmeric oleoresin, TO" is defined as an extract of turmeric in the form of viscous oily fluids, pasty semisolids or hard amorphous solids, and which comprise in varying concentrations, both curcuminoids and essential volatile oil, wherein the volatile oil comprises a mixture of non-curcuminoids in varying concentrations.

The term "Turmeric oil, TOIL" is defined as the essential volatile oil comprising a mixture of non-curcuminoids in varying concentrations.

The term, "curcumin removed turmeric oleoresin, CRTO" is defined as mother liquor obtained after at least one extraction of curcumin from TO which after removal of residual solvent used in extraction process, comprises the essential volatile oil containing a mixture of non-curcuminoids and may also comprise varying concentrations of curcuminoids.

The term, Hydrophilic-Lipophilic balance "HLB" is defined as the relative efficiency of the hydrophilic portion of the surfactant molecule to its lipophilic portion of the same molecule.

The term "emulsifier" is defined as an emulsifying agent compound or substance that acts as a stabilizer for emulsions. An emulsion is a mixture of two or more liquids that are normally immiscible. The emulsifier prevents immiscible liquids from separating from each other in the mixture. Emulsifier may also be defined as a type of surfactant.

The term "oil in water emulsifier" is defined an emulsifying agent compound or substance that acts as a stabilizer for oil-in-water emulsion, wherein the oil is the dispersed phase, and water is the continuous phase.

The term "non-ionic oil in water emulsifier" is defined an emulsifying agent compound or substance that acts as a stabilizer for oil-in-water emulsion, wherein the hydrophilic portion of the emulsifying substance does not contain an ionic group.

The term, emulsifier, surfactant may be used interchangeably unless otherwise stated differently.

The term lipophilic solvent is defined as substance which can dissolve other lipophilic substances.

The term solvent is defined as a liquid which can dissolve other substances.

The term pharmaceutically acceptable excipients is defined as substances other than the active pharmaceutical ingredient (API) that have been appropriately evaluated for safety and are intentionally included in a drug delivery system which facilitate processing of the drug formulation during its manufacture; protect, support, and/or enhance stability, bioavailability, or patient acceptability; facilitate in the effectiveness and/or delivery of the drug formulation and assist in maintaining the integrity of the drug formulation during its storage across its shelf life.

The term adsorbent is defined as solids which have capability of binding particles from liquids on their surface.

The term diluents or fillers or binders is defined as pharmaceutically acceptable excipients which provide the desired physical and functional properties to the drug/medical product formulation.

The term carrier is defined as pharmaceutically acceptable excipients which are designed to interact with and enhance the properties of active pharmaceutical ingredient—API.

In an embodiment, the present invention relates to water-soluble curcuma formulation comprising CRTO, curcuminoids and emulsifier or its pharmaceutically acceptable salts or its derivatives without pH buffer. In some embodiment, the invention relates to a water-soluble curcuma formulation comprising TO, curcuminoids and emulsifier or its pharmaceutically acceptable salts or its derivatives without pH buffer.

In an embodiment, the curcuma formulation comprises:
1 to 10% w/w curcumin and/or its metabolites in the composition;
5 to 70% w/w of CRTO;
30 to 45% w/w of a non-ionic emulsifier;
0.01% to 90% w/w of one or more other pharmaceutically acceptable excipients or carriers.

In an embodiment, the curcuma formulation comprises:
1 to 10% w/w curcumin and/or its metabolites in the composition;
5 to 70% w/w of TOIL;
30 to 45% w/w of a non-ionic emulsifier;
0.01% to 90% w/w of one or more other pharmaceutically acceptable excipients or carriers.

In an embodiment, the curcuma formulation comprises:
1 to 10% w/w curcumin and/or its metabolites in the composition;
5 to 70% w/w of TO;
30 to 45% w/w of a non-ionic emulsifier;
0.01% to 90% w/w of one or more other pharmaceutically acceptable excipients or carriers.

In an embodiment, the present invention relates to a water-soluble curcuma formulation comprising of ultrafine and fine particles loaded with a curcuminoid and a non-curcuminoid that are therapeutically safe.

In some embodiments, the present invention relates to a water-soluble curcuma formulation comprising TO and curcuminoids with ultrafine and fine particles that are therapeutically safe.

In some embodiments, the present invention relates to a water-soluble curcuma formulation comprising CRTO and curcuminoids with ultrafine and fine particles that are therapeutically safe.

In an embodiment, the curcuma formulation comprises ultrafine and fine particles of TOIL and curcuminoids that are therapeutically safe.

In an embodiment, the curcuma formulation comprises ultrafine and fine particles of TO, CRTO, TOIL and curcuminoids that are therapeutically safe.

In an embodiment, the average particle size in the curcuma formulation can be between approximately 40 nm and 200 nm. In some embodiments, the average particle size in the curcuma formulation can be between 40 nm and 100 nm. In some embodiments, the average particle size in the curcuma formulation can be between approximately 40 nm and 300 nm. In some embodiments, the average particle size in the curcuma formulation can be between approximately 40 nm and 500 nm. In some embodiments, the average particle size in the curcuma formulation composition can be between approximately 40 nm and 1000 nm. In some embodiments, the average particle size in the curcuma formulation can be between 40 nm and 2500 nm. In some embodiments, the average particle size in the curcuma formulation can be between approximately 201 nm and 300 nm. In some embodiments, the average particle size in the curcuma formulation can be between approximately 301 nm and 400 nm. In some embodiments, the average particle size in the curcuma formulation composition can be between approximately 401 nm and 500 nm. In some embodiments, the average particle size in the curcuma formulation can be between approximately 501 nm and 1000 nm. In some embodiments, the average particle size in the curcuma formulation can be between approximately 1001 nm and 2000 nm. In some embodiments, the average particle size in the curcuma formulation can be a combination of ultrafine particles in the range of 40 nm to 100 nm and fine particles in the range of 100 nm and 2500 nm In some aspect, blank ultrafine and fine particles lacking curcuminoid and/or non-curcuminoid can be present in the curcuma formulation.

In an embodiment, CRTO comprises a mixture of non-curcuminoids and/or residual amounts of curcuminoids after extraction from TO. In some embodiment, CRTO comprises Demethoxycurcumin, Bisdemethoxycurcumin, Aromatic turmerone, Beta-trans-Franesene, Aromatic curcumene, Curlone, Alpha-Zingiberene, Beta-Bisabolene, Caryophyllen oxide, Alpha-Phellandrene, Beta-Cymene, 1,8-Cineole, Trans-Ocimene, Alpha-Terpineol, Dehydrocurcumene, Hexadecanoic acid and Heptadecanic acid and/or their mixtures thereof.

In an embodiment, TO or CRTO comprises a mixture of sesquiterpenes, monomeric phenylpropenes, diarylpentanoids, diarylheptanoids containing curcumin free compounds such as tetrahydrocurcumin, cyclocurcumin and/or their mixtures thereof, monoterpenes, steroids, alkaloids, diterpenes, triterpenoids, fatty acids, sugar, proteins, carbohydrates, fiber, minerals, resin and/or their mixture thereof. In some embodiment, non-curcuminoids comprises a mixture of turmerone, turmeronol, turmerone, turmerine, himachalane, bergamotane, aristolene, silinanes, carbrane, cedrane, dihydrozingerone, sesquisabinane, sesquiphellandrene, curcumene, elemene, bisacurone, curdione, cyclocurcumin, germacrone, furanodiene, curcumol, calebin A, acrone, santalane, guaiane, curlone, carvacrol, limonene, tetrahydrocurcumin, hexahydrocurcumin, octahydrocurcumin, ferulic acid, in the form of an essential oil and/or their mixture thereof.

In an embodiment, the amount of a curcumin and/or its metabolites in the CRTO varies from 1 to 50% w/w, and the amount of non-curcuminoids in the CRTO varies from 49 to 99% w/w. In some embodiment, the amount of a curcumin and/or its metabolites in the CRTO varies from 1 to 50% w/w, and the amount of turmerones in the CRTO varies from 5 to 40% w/w.

In an embodiment, TO comprises curcumin and/or its metabolites and non-curcuminoids, wherein the amount of curcumin and/or its metabolites varies from 1 to 95% and amount of non-curcuminoids varies from 05 to 99%. In some embodiment, TO comprises curcumin and/or its metabolites and turmerones, wherein the amount of curcumin and/or its metabolites varies from 1 to 50% and amount of turmerones varies from 5 to 40%.

In an embodiment, TOIL or EVO comprises curcumin and/or its metabolites and non-curcuminoids, wherein the amount of curcumin and/or its metabolites varies from 1 to 15% and amount of non-curcuminoids varies from 5 to 75%. In some embodiment, TOIL comprises curcumin and/or its metabolites and turmerones, wherein the amount of curcumin and/or its metabolites varies from 1 to 10% and amount of turmerones varies from 5 to 40%.

In an embodiment, the invention relates to a water-soluble curcuma formulation comprising CRTO and curcuminoids or its pharmaceutically acceptable salts or its derivatives with improved stability as a self-nanoemulsifying formulation. In some embodiment, the present invention relates to a water-soluble curcuma formulation comprising TO and curcuminoids with improved biostability as a self-nanoemulsifying formulation. In some embodiment, the present invention relates to a water-soluble curcuma formulation comprising TOIL or EVO and curcuminoids with improved biostability as a self-nanoemulsifying formulation. In some embodiment, the present invention relates to a water-soluble curcuma formulation comprising TOIL or EVO, TO, CRTO and curcuminoids with improved biostability as a self-nanoemulsifying formulation.

In an embodiment, the composition comprises non-ionic emulsifier. In some embodiment, the composition comprises non-ionic oil in water emulsifier.

In an embodiment, amount of emulsifier varies from 30 to 45% w/w of the curcuma formulation.

In an embodiment, non-ionic oil-in-water emulsion has high HLB value for good water solubility. The HLB value of non-ionic emulsion is between 9 and 18 and more preferably between 11 and 16. In some embodiment, emulsifier in the present disclosure can be used alone or in combination to maintain total HLB of the curcuma formulation between 9 to 18.

In an embodiment of the present disclosure, non-ionic oil-in-water emulsifier are selected but not limited to group comprising polyoxyethylene products of hydrogenated vegetable oils such as commercially available Dalda, Margarine, polyethoxylated castor oils, polyethoxylated hydrogenated castor oil, polyoxyethylene-sorbitan-fatty acid esters, polyoxyethylene castor oil derivatives or a combination thereof, commercially available as Kolliphor®, such as Kolliphor® EL (PEG-35 castor oil), Kolliphor® RH40 (PEG-40 hydrogenated castor oil), Kolliphor® RH60 (PEG-60 hydrogenated castor oil), Labrasol® (PEG-8 Caprylic/Capric Glycerides), Gelucire® (Stearoyl polyoxylglycerides), Polysorbates, PLURONIC® L-64 and L-127 (block copolymers based on ethylene oxide and propylene oxide), TRITON™ X 100 (Polyethylene glycol tert-octylphenyl ether), SIMULSOL™ (polyoxyethylated products comprising Polyoxyethylated lauric alcohol, Polyoxyethylated cetostearyl alcohol, Polyoxyethylated stearic acid and like), NIKKOL™ HCO-50 (Polyoxyethylene (50) hydrogenated castor oil), NIKKOL™ HCO-35 (Polyoxyethylene (35) hydrogenated castor oil), NIKKOL™ HCO-40 (Polyoxyethylene (40) hydrogenated castor oil), NIKKOL™ HCO-60 (Polyoxyethylene (60) hydrogenated castor oil), TWEENS® (Polysorbates) and/or their mixture thereof.

In an embodiment, the solvent is selected from a group comprising ethyl alcohol, isopropyl alcohol, glycofurol, polyethylene glycol (PEG 200, 400), glycerol, polypropylene glycol, propylene glycol, N-methyl-2-pyrolidone and ethyl alcohol and/or mixture thereof.

In an embodiment, the lipophilic solvent are selected from, but not limited to fractionated oil, Caprylic triglyceride, Capric triglyceride and/or an oil containing medium chain fatty acid triglycerides that herein is defined as triglycerides with two or three fatty acids having an aliphatic chain of 8 to 12 carbon atoms, CAPTEX 300, isopropyl myristate, isopropyl palmitate, ethyl linoleate, Ethyl oleate esters of fatty acids, propylene glycol dicaprylate, propylene glycol dilaurate or oils containing propylene glycol di fatty acid esters and/or their mixtures thereof.

In an embodiment, the lipophilic solvent varies from 50 to 200% w/w of curcumin. In some embodiment, the lipophilic solvent varies from 5 to 70% w/w of composition.

In an embodiment, the composition contains suitable and pharmaceutically acceptable excipients but not limited to adsorbent, diluent, filler, sweetener, flavoring agent, polymers, carrier, gelling agent, stabilizer, surfactant, plasticizer, lubricant, reducing agent, buffer agent, sweetening agent, base, corrigent, binder, suspending agent, antioxidant, polish, coating, wetting agent, gelling agent, wet modifier, filler, antifoaming agent, refrigerate agent, coloring matter, flavoring agent, perfume, sugar coating agent, isochronizing agent, softener, emulsifying agent, foaming agent, pH modifier, anti-frothing agent, flavoring agents, preservatives, diluent, excipient, dispersing agent, disintegrator, fragrance, desiccant, antiseptics, preservative, solubilizing agent, solubilizer, solvent, superplasticizer, antistatic agent, extender, moisturizing agent, and the like.

In an embodiment, adsorbent is selected but not limited to PEG 6000, maltodextrin, starch, hydrolysed starches, Fibers (soluble oligo saccharides from plants such as Chicory), Dextran, Celluloses, copolymers of polyvinylpyrrolidone, sugar alcohols like iso-malt, sorbitol, xylitol or mannitol, cellulose derivatives (such as hydroxypropylmethyl cellulose (HPMC) and/or hydroxypropyl cellulose (HPC)), cyclodextrines and its derivatives and combinations thereof. In some embodiment, adsorbents are PEG 6000 (melted at 60° C.) and/or Maltodextrin.

In an embodiment, a diluent or a filler or a binder is selected but not limited to mannitol, sorbitol, lactose, hard boiled candy, confectioner's sugar. In some embodiment, a diluent or a filler or a binder is mannitol or sorbitol.

In an embodiment, carrier are water soluble polymers but not limited to polyglutamic acid, Polyethylene glycol, propylene glycol, glycerol, propylene glycol esters, polyglycerol oleate polyvinyl alcohol, non-ethoxylated polymers like Glyceryl Stearate (and) Polyglyceryl-6 Palmitate/Succinate (and) Cetearyl Alcohol (NatraGem™ EW) and N-(2-Hydroxypropyl) methacrylamide (PHPMA). Polyethylene glycols could have a number average molecular weight of about 300, 350, 400, 450, 500, 550, 600, 650, 700, 750, 800, 850, 900, 950 and 1000.

In an embodiment, a gelling agent is selected from but not limited to carboxymethyl cellulose, ethylcellulose, gelatin, hydroxyethyl cellulose, hydroxypropyl cellulose, magnesium aluminum silicate, methylcellulose, poloxamers, polyvinyl alcohol, sodium alginate, tragacanth, and xanthan gum.

In an embodiment, the composition can be taken orally in the form of a of a solid (e.g., tablet or pill), a liquid (e.g., solution, suspension or lotion), or semisolid (e.g., gel, cream or ointment) or liquid drops or powder or capsules. In some embodiments, these compositions be delivered orally and the components be prepared for ingestion in a manner that makes the composition available in therapeutically effective amounts. As such, they may be prepared as water soluble compositions, delivered in liquid form, lyophilized, encapsulated, or in a manner suitable for time release, delayed release or enteric delivery, or any manner typically used for orally delivered pharmaceuticals, nutraceuticals or vitamins, or combined with foods or other normally ingested products. In some embodiment orally soluble tablet dissolve within 15 to 30 minutes under tongue or buccal cavity. In some embodiment, orally soluble tablet is a lozenge. In some embodiment, lozenges dissolves when placed in buccal cavity and could be sucked to give its effect in and around Pharynx (throat). In some embodiment, lozenges dissolves during the period of about five minutes. In some embodiment, composition can be delivered by nasal spray, inhalation techniques, transdermally, transmucossally, ocularly, by suppository, injected, or by intravenous methods. In some embodiment, composition in combination with other nutraceuticals, vitamins, amino acids, proteins, dietary fibres, natural products like honey can be delivered as orally consumable Anti-hangover or Health drinks.

In an embodiment, the composition can be used for the treatment of different conditions of humans but not limited to pro-inflammatory diseases including cancer, cardiovascular disease, arthritis, uveitis, ulcerative proctitis, Crohn's disease, ulcerative colitis, irritable bowel disease, tropical pancreatitis, peptic ulcer, gastric ulcer, idiopathic orbital inflammatory pseudotumor, oral lichen planus, gastric inflammation, vitiligo, psoriasis, acute coronary syndrome, atherosclerosis, diabetes, diabetic nephropathy, diabetic microangiopathy, lupus nephritis, renal conditions, acquired immunodeficiency syndrome, β-thalassemia, biliary dyskinesia, Dejerine-Sottas disease, cholecystitis, and chronic bacterial prostatitis.

In another embodiment of the present disclosure, a process for preparing composition is disclosed. In an embodiment, composition can be formulated by techniques including, but not limited to, nano/micro precipitation, which can be carried out by methods such as sonication, emulsification, solvent titration, milling, spray drying, solid dispersion, hot-melt extrusion, freeze drying methods, or supercritical fluid technology.

In one embodiment of the present disclosure, the process for preparation of water-soluble curcuma liquid drops comprising of steps:
  a. mixing curcumin, TO or CRTO or TOIL or a combination thereof, non-ionic oil in water emulsifier and a solvent to form a uniform blend;
  b. sonicating blend of step (a) for ten seconds at a time and resting for thirty seconds alternatingly to obtain clear solution; and
  c. diluting clear solution in aqueous medium to obtain desired concentration of curcuma drops.

In one embodiment of the present disclosure, the process for preparation of water-soluble curcuma powder comprising of steps:
  a. mixing curcumin, TO or CRTO or TOIL or a combination thereof, and a non-ionic emulsifier to form a uniform blend;
  b. sonicating the blend of step (a) for ten seconds at a time and resting for thirty seconds alternatingly to obtain a thick paste;
  c. adding an adsorbent to the paste of step (b) under continuous stirring to obtain a mixture;
  d. cooling the mixture of step (c) obtaining a dry brittle mass;
  e. pulverizing the dry brittle mass obtaining a water-soluble curcuma powder; and
  f. packing the water-soluble curcuma powder.

In one embodiment of the present disclosure, the process for preparation of water-soluble curcuma formulation comprising of steps:
  a. mixing curcumin, TO or CRTO or TOIL or a combination thereof and non-ionic emulsifier to form a uniform blend;
  b. sonicating the blend of step (a) for ten seconds at a time and resting for thirty seconds alternatingly to obtain thick paste;
  c. adding an adsorbent to the paste of step (b) under continuous stirring to obtain a mixture; d. cooling the mixture of step (c) to obtain a dry brittle mass;
  e. pulverizing the dry brittle mass, obtaining a powder;
  f. adding pharmaceutically acceptable diluents or fillers or binders and sweeteners and flavouring agents to the obtained powder, mixing, blending to obtain a blended mixture;
  g. compressing the blended mixture to produce conventional and/or water-soluble tablets/lozenges;
  packaging of the water-soluble curcuma tablets/lozenges;
  h. dissolving the tablets obtained in step (g) in appropriate quantity of purified water to obtain water soluble liquid, and
  i. packaging the water-soluble curcuma liquid.

In one embodiment of the present disclosure, the process for preparation of transdermal curcuma patches comprising steps:
  a. mixing curcumin, TO or CRTO or TOIL or a combination thereof and nonionic emulsifier to form a uniform blend;
  b. sonicating blend of step (a) for ten seconds at a time and resting for thirty seconds alternatingly to obtain a thick paste; adding an adsorbent to the thick paste of step (b) under continuous stirring; preparing a solvent mixture by mixing a solvent such as ethanol and methylene chloride;
  c. preparing a polymer mixture by mixing hydroxy propyl methylcellulose and ethyl cellulose in mortar & pestle;
  d. adding third portion quantity of the solvent mixture of step (d) to the polymer mixture;
  e. homogenizing the polymer mixture until a uniform polymer solution is obtained;
  f. mixing diethyl phthalate to the above polymer solution of step (e), mixing the sonicated mixture of step b to obtained mixture until uniform solution or dispersion obtained, make up final volume of the obtained solution or dispersion, pouring the resultant solution into a vessel such as 9 cm diameter plastic Petri plate (pre-fixed aluminum foil on to the base of the Petri plate as a backing membrane) without forming air bubbles and distributing uniformly on to entire circumference of the Petri plate, drying the above solution at room temperature for 8-10 hours or kept in the dryer at 40° C. until completely dry film obtained, the peeled film is obtained with one side of aluminum foil as the backing membrane.

In one embodiment of the present disclosure, the process for preparation of water-soluble curcuma drops comprising of steps:
a. mixing curcumin, TO or CRTO or TOIL or a combination thereof, medium chain triglycerides, non-ionic emulsifier, an adsorbent and a solvent to form a blend;
b. sonicating the blend of step (a) for ten seconds at a time and resting for thirty seconds alternatingly, obtaining clear solution;
c. and diluting clear solution in aqueous medium to obtain desired concentration of curcuma drops.

In one embodiment of the present disclosure, the process for preparation of water-soluble curcuma powder comprising steps:
a. mixing curcumin, TO or CRTO or TOIL or a combination thereof, medium chain triglycerides, and non-ionic emulsifier to form a blend;
b. sonicating blend of step (a) for ten seconds at a time and resting for thirty seconds alternatingly, obtaining a thick curcumin paste;
c. mixing curcumin paste of step (b) with an adsorbent such as PEG-6000 melted at 60° C., allowing to cool, obtaining a dry brittle mass;
d. pulverizing dry brittle mass of step (c) to obtain water-soluble curcuma powder.

In one embodiment of the present disclosure, the process for preparation of water-soluble curcuma tablets comprising steps:
a. mixing curcumin, TO or CRTO or TOIL or a combination thereof, medium chain triglycerides, non-ionic emulsifier and dispersing in solvent;
b. sonicating blend of step (a) for ten seconds at a time and resting for thirty seconds alternatingly to obtain thick curcumin paste;
c. mixing curcumin paste of step (b) with adsorbent such as PEG-6000 melted at 60° C., allowing to cool, obtaining a dry brittle mass;
d. pulverizing dry brittle mass of step (c) to obtain water-soluble curcuma powder;
e. adding pharmaceutically acceptable excipients in curcuma powder of step (d) to obtain tablets.

The invention is illustrated by the following working examples in which all parts and amounts are by weight unless otherwise stated. The following examples as described are not intended to be construed as limiting the scope of the present invention.

WORKING EXAMPLES

Example 1

The composition of the curcuma liquid drops with ethanol as base is shown in Table 1.

TABLE 1

Composition of the curcuma liquid drops of Example 1 (herein after referred as sample 1)

| Ingredient | % w/v |
| --- | --- |
| Curcumin 95%* | 5.00 (5.25% Drug is used to compensate 95% of curcuminoids content to 100%) |
| CRTO | 8.40 |
| Kolliphor EL | 46.42 |

TABLE 1-continued

Composition of the curcuma liquid drops of Example 1 (herein after referred as sample 1)

| Ingredient | % w/v |
| --- | --- |
| Ethanol | 42.48 |
| Sucralose | 0.10 |

*"Curcumin (95%)" means a mixture of curcuminoids having at least 95 wt % of the curcuminoids.

The curcuma liquid drops of the sample 1 was formulated according to following process steps:

Step 1: Take Kolliphor EL and add CRTO under stirring. Heat the mixture under stirring till it attains the required temperature between 80° C.-120° C. Add curcumin powder slowly to this mixture under continuous stirring with the temperature maintained between 80° C.-120° C. Continue stirring for 5 minutes subsequent to completion of addition of Curcumin. Remove the heat application once dark brown colour solution is observed and continue stirring till the temperature of mixture drops down to 40° C.

Step-2: Take Sucralose and dissolve in specified quantity of ethanol under stirring. Continue stirring for 10 minutes.

Step-3: Add Step-2 to step-1 slowly and continue stirring for 10 minutes.

Step-4: Carry out the Sonication using sonicator (UP200st Ultrasonic processor, Hielscher, Germany) for the bulk of Step-3 with the following parameters.
Sonotrode—As per batch size.
Energy: 50000 watts.
Temperature cut off: 40° C.
On time cycle: 10-20 sec.
Off time cycle: 20-30 sec.
No of cycles: Till the specified Energy is imparted to the mixture.

Step-7: Pack the obtained Curcuma liquid drops in suitable drop dispensing bottles.

Example 2

The composition of the curcuma liquid drops with propylene glycol (PG) as base is shown in Table 2.

TABLE 2

Composition of the curcuma liquid drops of Example 2 (herein after referred as sample 2)

| Ingredient | % w/v |
| --- | --- |
| Curcumin 95% | 5.00 (5.25% Drug is used to compensate 95% of curcuminoids content to 100%) |
| CRTO | 8.40 |
| Kolliphor EL | 46.42 |
| Propylene glycol | 42.07 |
| Sucralose | 0.10 |
| HPMC E-5 | 0.23 |
| Purified water | 4.72 |

The curcuma liquid drops of sample 2 was formulated according to following process steps:

Step-1: Take Kolliphor EL and add CRTO under stirring. Heat the mixture under stirring till it attains the required temperature between 80° C.-120° C. Add curcumin powder slowly to this mixture under continuous stirring with the temperature maintained between 80° C.-120° C. Continue stirring for 5 minutes subsequent to completion of addition of Curcumin. Remove the heat application once dark brown colour solution is observed and continue stirring till the temperature of mixture drops down to 40° C.

Step-2: Take HPMC E-5 and disperse in specified quantity of purified water under stirring. Continue stirring for 5 minutes.

Step-3: Add Step-2 to step-1 slowly under stirring. Continue stirring for 5 minutes.

Step-4: Take specified quantity of Sucralose and Add to the bulk of step-3 under stirring. Continue stirring for 10 minutes.

Step-5: Take specified quantity of Propylene glycol and Add to the bulk of step-4 under stirring. Continue stirring for 15 minutes.

Step-6: Carry out the sonication using sonicator (UP200st Ultrasonic processor, Hielscher, Germany) for the bulk of Step 5 with the following parameters.
Sonotrode—As per batch size.
Energy: 50000 watts.
Temperature cut off: 40° C.
On time cycle: 10-20 sec.
Off time cycle: 20-30 sec.
No of cycles: Till the specified Energy is imparted to the mixture Step-7: Pack the obtained Curcuma liquid drops in suitable drop dispensing bottles.

Example 3

The composition of the curcuma liquid drops with polyethylene glycol (PEG) is shown in Table 3.

TABLE 3

Composition of the curcuma liquid drops of Example 3 (herein after referred as sample 3)

| Ingredient | % w/v |
| --- | --- |
| Curcumin 95% | 5.00 (5.25% Drug is used to compensate 95% of curcuminoids content to 100%) |
| CRTO | 8.40 |
| Kolliphor EL | 46.42 |
| PEG-400 | 43.00 |
| Sucralose | 0.10 |
| HPMC E-5 | 0.23 |
| Purified water | 4.72 |

The curcuma liquid drops of the sample 3 was formulated according to following process steps:

Step-1: Take Kolliphor EL and add CRTO under stirring. Heat the mixture under stirring till it attains the required temperature between 80° C.-120° C. Add curcumin powder slowly to this mixture under continuous stirring with the temperature maintained between 80° C.-120° C. Continue stirring for 5 minutes subsequent to completion of addition of Curcumin. Remove the heat application once dark brown colour solution is observed and continue stirring till the temperature of mixture drops down to 40° C.

Step-2: Take HPMC E-5 and disperse in specified quantity of purified water under stirring. Continue stirring for 5 minutes.

Step-3: Add Step-2 to step-1 slowly under stirring. Continue stirring for 5 minutes.

Step-4: Take specified quantity of Sucralose and Add to the bulk of step-3 under stirring. Continue stirring for 10 minutes.

Step-5: Take specified quantity of PEG-400 and Add to the bulk of step-4 under stirring. Continue stirring for 15 minutes.

Step-6: Carry out the sonication using sonicator (UP200st Ultrasonic processor, Hielscher, Germany) for the bulk of Step-5 with the following parameters.
Sonotrode—As per batch size.
Energy: 50000 watts.
Temperature cut off: 40° C.
On time cycle: 10-20 sec.
Off time cycle: 20-30 sec.
No of cycles: Till the specified Energy is imparted to the mixture Step-7: Pack the obtained Curcuma liquid drops in suitable drop dispensing bottles.

Example 4

Curcuma liquid drops with increased level of curcumin infusion in CRTO & PEG 400. The composition of the curcuma liquid drops with PEG 400 is shown in Table 4.

TABLE 4

Composition of the curcuma liquid drops of Example 4 (herein after referred as sample 4)

| Ingredient | % w/v |
| --- | --- |
| Curcumin 95% | 5.00 (5.25% Drug is used to compensate 95% of curcuminoids content to 100%) |
| CRTO | 8.40 |
| Curcumin infused with CRTO Oil | 1.00 |
| Kolliphor EL | 44.00 |
| PEG-400 | 42.00 |
| Curcumin infused with PEG-400 | 9.49 |
| HPMC E-5 | 0.23 |
| Purified water | 5.00 |

The curcuma liquid drops of the sample 4 was formulated according to following process steps:

Step-1: Take Kolliphor EL and add CRTO (Infused with 10% Curcumin) under stirring. Heat the mixture under stirring till it attains the required temperature between 100° C.-120° C. Add curcumin powder slowly to this mixture under continuous stirring with the temperature maintained between 100° C.-120° C. Continue stirring for 5 minutes subsequent to completion of addition of Curcumin.

Step-2: Take HPMC E-5 and disperse in specified quantity of purified water under stirring. Continue stirring for 5 minutes.

Step-3: Add Step-2 to step-1 slowly and under stirring with the temperature between 100° C.-120° C. Continue stirring for 5 minutes.

Step-4: Take PEG-400 and heat it under continuous stirring till it attains the required temperature between 100° C.-120° C. Add the specified Curcumin slowly under continuous stirring with the temperature maintained between 100° C.-120° C. Continue stirring for 5 minutes.

Step-5: Add Step 4 to Step 1 slowly, under continuous stirring with the temperature maintained between 100° C.-120° C. Remove heat application and continue stirring till the temperature of mixture drops down to 70° C.

Step 6: Carry out the sonication using sonicator (UP200st Ultrasonic processor, Hielscher, Germany) for the bulk of Step 5 with the following parameters.
Sonotrode—As per batch size.
Energy: 150000 watts.
Temperature cut off: 120° C.
On time cycle: 10-20 sec.
Off time cycle: 20-30 sec.
No of cycles: Till the specified energy is imparted to the mixture
Step-7: Pack the obtained Curcuma liquid drops in suitable drop dispensing bottles Example 5

The various batch formulas of curcuma liquid drops are shown in Table 5.

TABLE 5

Composition of various batch formulas of curcuma liquid drops of Example 5.
Curcumin Nanodrops 50 mg/ml

| | Sample No. | | | | | | | | | | | |
|---|---|---|---|---|---|---|---|---|---|---|---|---|
| | 05 | 06 | 07 | 08 | 09 | 010 | 011 | 012 | 013 | 014 | 015 | 016 |
| Batch size | 5.0 L | 0.1 L | 0.1 L | 0.1 L | 0.1 L | 2.5 L | 2.5 L | 2.0 L | 0.2 L | 1.0 L | 1.2 L | 1.0 L |
| Ingredient | mg/mL | mg/mL | mg/mL | mg/mL | mg/mL | mg/mL | mg/mL | mg/mL | mg/mL | mg/mL | mg/mL | mg/mL |
| Curcumin | 52.63 | 52.63 | 52.63 | 52.63 | 52.63 | 52.63 | 52.63 | 52.52 | 52.52 | 52.52 | 52.52 | 52.52 |
| CRTO | X | 100 | 100 | 84 | 84 | 84 | 84 | 84 | 84 | 84 | 84 | 84 |
| Captex-300 Caprylic/Capric triglyceride | 0.1 | X | X | X | X | X | X | X | 0.1 | X | X | X |
| Ethanol | 424.8 | 424.8 | X | 424.8 | 424.8 | 424.8 | 424.8 | X | X | 424.8 | X | 424.8 |
| Kolliphor EL (PEG-35 Castor oil) | 440 | 464.2 | 464.2 | 464.2 | 464.2 | 464.2 | 464.2 | 464.2 | 464.2 | 464.2 | 464.2 | 464.2 |
| Propylene Glycol | X | X | X | X | X | X | X | Q.S | Q.S | X | 420.79 | X |
| Sucralose | 0.017 | 1.0 | X | 0.5 | 0.5 | 1.0 | 1.0 | 1.0 | 1.0 | 1.0 | 1.0 | 1.0 |
| Cardamom | 0.025 | X | X | X | X | X | X | X | X | X | X | X |
| Black pepper | X | X | X | X | 1 | X | X | X | X | X | X | X |
| Menthol | X | X | X | 0.1 | X | X | X | X | X | X | X | X |
| HPMC E-5 | X | X | X | X | X | X | X | X | X | X | 2.36 | X |
| Purified water | X | X | X | X | X | X | X | X | X | X | 47.24 | X |
| Observation | Dark yellowish brown colour solution. Precipitation/ sedimentation observed | | | | Dark yellowish brown colour solution. Precipitation/ sedimentation not observed | | | Dark yellowish brown colour solution. Precipitation/ sedimentation observed | | Dark yellowish brown colour solution. Precipitation/ sedimentation not observed | |
| pH | — | — | — | — | — | 6.73 | 6.81 | — | — | — | 6.30 | — |
| Wt/ml | — | — | — | — | — | 0.91 | 0.95 | — | — | — | 1.01 | — |

The operating procedure of sonicator, for all samples executed for the Example 5 were kept same during manufacture. Sonicator was operated according to following procedure:
I. Switch on the instrument by connecting plug.
II. Press the black colour button and touch the 'SETTING' which displays on screen and start to set the above-mentioned parameters by using arrow '▲' to go upside & the '▼' to come downside. (Navigation options '▲' & '▼').
III. Select the Limit type by touching on 'ENERGY' which will display on screen.
IV. Set the energy to 50000 watts by using the arrows '►' to decrease the energy and the arrow '◄' to increase energy.
V. After energy setting calibration will display on screen, it is not required for this process
VI. Set the stop mode by touching on 'PAUSE' which will display on screen.
VII. Set the Unit by touching on '° C. barg' which will display on screen.
VIII. Set the temperature control on by touching 'ON' which will display on screen.
IX. Set the upper temperature limit by using arrows (◄ ► ▼ ▲).
X. Set the lower temperature limit by using arrows (◄ ► ▼ ▲).
XI. Set the temperature Delta to 14° C. by using arrows (◄ ► ▼ ▲).
XII. Set the adjustment snap to 1% by using arrows (◄ ► ▼ ▲).
XIII. Set the analog input off by touching 'OFF' which will display on screen.
XIV. Set the Press control on by touching 'ON' which will display on screen.
XV. Set the maximum pressure 1000 psig and minimum pressure 0000 psig by using arrows (◄ ► ▼ ▲).
XVI. Set the remote control off by touching 'OFF' which will display on screen.
XVII. Set the SD interval Isec/10 sec by touching '1 sec/10 sec' which will display on screen.
XVIII. Set the Period clock on by touching 'ON' which will display on screen.
XIX. Set the on time 10 sec by using arrows (◄ ► ▼ ▲).
XX. Set the off time 30 sec by using arrows (◄ ► ▼ ▲).
XXI. Keep the IP Address as it is which is previously fixed.
XXII. Set the DHPC server on by touching 'ON' which will display on screen.
XXIII. Set the DHPC Client on by touching 'ON' which will display on screen.
XXIV. Set the clock if necessary, by using arrows (◄ ► ▼ ▲).

XXV. Set the date if necessary, by using arrows (◄ ► ▼ ▲).

XXVI. Finally press the black button to start the sonication once it completes remove from the sonication chamber check the physical observations and pH.

Various samples of Example 05 were manufactured according to following procedure:

Sample 05 of Example 05 was manufactured according to following procedure:

Step-1: Add sucralose and dissolve in ethanol manually.

Step-2: Disperse curcumin in Captex 300 and Kolliphor EL in a stainless-steel container and heat it at 80° C.-130° C. under manual stirring.

Step-3: Cool down the step-2 to room temperature. Add Step 1 to step 2 by maintaining temp 30° C.-35° C. Add cardamom flavour to step 2.

Step-4: Make up the volume with ethanol.

Step-5: Carry out the sonication under conditions shown in Table 6.

TABLE 6

Conditions adopted for sonication in sample 05 of Example 05.

| Sl. No. | Name of Parameter | Value |
| --- | --- | --- |
| 1 | Energy(watts) | 50000 |
| 2 | On time (Sec) | 10 |
| 3 | Off time (sec) | 30 |
| 4 | Upper temp (° C.) | 40 |
| 5 | Lower temp (° C.) | 0 |
| 6 | Sonotrode (mm) | 7 |

Sample 06 of Example 5 was manufactured according to following procedure:

Step-1: Take Kolliphor EL & CRTO in a stainless-steel container and heat it between 80° C.-120° C. under stirring at 1200-1400 rpm. Add curcumin powder slowly under continuous stirring at 1200-1400 rpm until dark brown colour solution is observed.

Step-2: Cool down the step-1 to room temperature.

Step-3: Add sucralose and dissolve in ethanol manually. Add this to Step 1 under stirring at 1200-1400 rpm.

Step-4: Carry out the sonication for step 1 under conditions shown in Table 07.

TABLE 07

Conditions adopted for sonication in sample 06 of Example 05.

| Sl. No. | Name of Parameter | Value |
| --- | --- | --- |
| 1 | Energy(watts) | 50000 |
| 2 | On time (Sec) | 10 |
| 3 | Off time (sec) | 20 |
| 4 | Upper temp (° C.) | 30 |
| 5 | Lower temp (° C.) | 0 |
| 6 | Sonotrode (mm) | 7 |

Sample 07 of Example 5 was manufactured according to following procedure:

Step-1: Take Kolliphor EL in a stainless-steel container and heat it between 80° C.-120° C. under stirring at 1200-1400 rpm. Add curcumin powder slowly under continuous stirring at 1200-1400 rpm until dark brown colour solution is observed.

Step-2: Cool down the step-1 to room temperature.

Step-3: Add CRTO slowly under manual stirring.

Step-4: Carry out the sonication for step 1 under conditions shown in Table 8.

TABLE 8

Conditions adopted for sonication in sample 07 of Example 05.

| Sl. No. | Name of Parameter | Value |
| --- | --- | --- |
| 1 | Energy(watts) | 50000 |
| 2 | On time (Sec) | 10 |
| 3 | Off time (sec) | 30 |
| 4 | Upper temp (° C.) | 40 |
| 5 | Lower temp (° C.) | 0 |
| 6 | Sonotrode (mm) | 7 |

Sample 08 of Example 5 was manufactured according to following procedure:

Step-1: Take Kolliphor EL & CRTO in a stainless-steel container and heat it at 40° C. under stirring at 1200-1400 rpm. Add curcumin powder slowly under continuous stirring at 1200-1400 rpm until dark brown colour solution is observed.

Step-2: Add sucralose, menthol and dissolve in ethanol manually.

Step-3: Cool down the step-1 to room temperature.

Step-4: Carry out the sonication for step 1 under conditions shown in Table 9.

TABLE 9

Conditions adopted for sonication in sample 08 of Example 05.

| Sl. No. | Name of Parameter | Value |
| --- | --- | --- |
| 1 | Energy(watts) | 50000 |
| 2 | On time (Sec) | 10 |
| 3 | Off time (sec) | 30 |
| 4 | Upper temp (° C.) | 40 |
| 5 | Lower temp (° C.) | 0 |
| 6 | Sonotrode (mm) | 7 |

Sample 09 of Example 5 was manufactured according to following procedure:

Step-1: Take Kolliphor EL & CRTO in a stainless-steel container and heat it between 80° C.-120° C. under stirring at 1200-1400 rpm. Add curcumin and black pepper powder slowly under continuous stirring at 1200-1400 rpm until dark brown colour solution is observed.

Step-2: Cool down the step-1 to room temperature.

Step-3: Add sucralose and dissolve in ethanol manually. Add this to Step 1 under stirring at 1200-1400 rpm.

Step-4: Carry out the sonication for step 1 under conditions shown in Table 10.

TABLE 10

Conditions adopted for sonication in sample 09 of Example 05.

| Sl. No. | Name of Parameter | Value |
| --- | --- | --- |
| 1 | Energy(watts) | 50000 |
| 2 | On time (Sec) | 10 |
| 3 | Off time (sec) | 30 |
| 4 | Upper temp (° C.) | 40 |
| 5 | Lower temp (° C.) | 0 |
| 6 | Sonotrode (mm) | 7 |

Samples 10, 11, 14 and 16 of Example 5 were manufactured according to following procedure:

Step-1: Take Kolliphor EL & CRTO in a stainless-steel container and heat it between 80° C.-120° C. under stirring at 1200-1400 rpm. Add curcumin powder slowly under continuous stirring at 1200-1400 rpm until dark brown colour solution is observed.

Step-2: Cool down the step-1 to room temperature under continuous stirring at 1200-1400 rpm.

Step-3: Add sucralose and dissolve in ethanol under stirring at 800-1000 rpm for 10 minutes. Add this to Step 2 under stirring at 1200-1400 rpm.

Step-3: Carry out the sonication for step 2 under conditions shown in Table 11.

TABLE 11

Conditions adopted for sonication in samples 10, 11, 14 and 16 of Example 05.

| Sl. No. | Name of Parameter | Value |
| --- | --- | --- |
| 1 | Energy(watts) | 50000 |
| 2 | On time (Sec) | 10 |
| 3 | Off time (sec) | 30 |
| 4 | Upper temp (° C.) | 40 |
| 5 | Lower temp (° C.) | 0 |
| 6 | Sonotrode (mm) | 7 |

Sample 12 of Example 5 was manufactured according to following procedure:

Step-1: Take Kolliphor EL & CRTO in a stainless-steel container and heat it. Once the temp of 65° C. is attained, add curcumin powder slowly under continuous stirring at 1800 rpm. Stir continuously at 1800 rpm for 30 min by maintaining the temperature of 80° C.-120° C.

Step-2: Cool down the step-1 to 40° C. under continuous stirring at 1900 rpm. Add sucralose and stir.

Step-3: Make up the volume with propylene glycol and stir at 2200 rpm for 30 min Step-4: Carry out the sonication under conditions shown in Table 12.

TABLE 12

Conditions adopted for sonication in sample 12 of Example 05.

| Sl. No. | Name of Parameter | Value |
| --- | --- | --- |
| 1 | Energy(watts) | 50000 |
| 2 | On time (Sec) | 10 |
| 3 | Off time (sec) | 30 |
| 4 | Upper temp (° C.) | 40 |
| 5 | Lower temp (° C.) | 0 |
| 6 | Sonotrode (mm) | 7 |

Sample 13 of Example 5 was manufactured according to following procedure:

Step-1: Take Kolliphor EL, Captex 300 & CRTO oil in a stainless-steel container and heat it between 80° C.-120° C. under stirring at 1800 rpm. Add curcumin powder slowly under continuous stirring at 1800 rpm until dark brown colour solution is observed.

Step-2: Cool down the step-1 to 40° C. under continuous stirring at 1800-1900 rpm. Add sucralose and stir for 10 minutes.

Step-3: Make up the volume with propylene glycol and stir at 1800-1900 rpm for 15 min.

Step-4: Carry out the sonication under the conditions shown in Table 13.

TABLE 13

Conditions adopted for sonication in sample 13 of Example 05.

| Sl. No. | Name of Parameter | Value |
| --- | --- | --- |
| 1 | Energy(watts) | 50000 |
| 2 | On time (Sec) | 10 |
| 3 | Off time (sec) | 30 |
| 4 | Upper temp (° C.) | 40 |
| 5 | Lower temp (° C.) | 0 |
| 6 | Sonotrode (mm) | 7 |

Sample 15 of Example 5 was manufactured according to following procedure:

Step-1: Take IPMC E-5 and disperse in purified water by stirring at 700-900 rpm and keep it aside for 30 minutes for swelling.

Step-2: Take Kolliphor EL & CRTO in a stainless-steel container and heat it between 80° C.-120° C. under stirring at 1200-1400 rpm. Add curcumin powder slowly under continuous stirring at 1200-1400 rpm until dark brown colour solution is observed.

Step-3: Add Propylene glycol into step-2 under stirring at 1200-1400 rpm for 10 minutes and then add sucralose under stirring at 1200-1400 rpm. Cool down the step-2 to room temperature.

Step-3: Add Step-1 to step-2 with stirring at 1200-1400 rpm.

Step-4: Carry out the Sonication for step 2 under conditions shown in Table 14.

TABLE 14

Conditions adopted for sonication in sample 15 of Example 05.

| Sl. No. | Name of Parameter | Value |
| --- | --- | --- |
| 1 | Energy(watts) | 50000 |
| 2 | On time (Sec) | 10 |
| 3 | Off time (sec) | 30 |
| 4 | Upper temp (° C.) | 40 |
| 5 | Lower temp (° C.) | 0 |
| 6 | Sonotrode (mm) | 7 |

It was observed that physical property of end product of different sample nos. in Example 05 varied. Samples Nos. 05, 06, 07, 12 and 13 showed precipitation/sedimentation. Sample Nos. 08 and 09 showed no precipitation/sedimentation but are with flavours. Sample Nos. 10, 11, 14 and 16 showed no precipitation/sedimentation but are without flavours and with ethanol. Sample No. 15 showed no precipitation/sedimentation but are without flavours and with Propylene Glycol & HPMC.

Example 6

The composition of curcuma liquid drops of Example 6 is shown in Table 15.

TABLE 15

Composition of curcuma drops of Example 6.

| Ingredients | Each ml contains | Qty. for 2 litres |
| --- | --- | --- |
| Curcumin (95%) | 52.63 mg | 105.26 g |
| Ethanol | 0.4248 ml (QS to 1 ml) | 400.00 g |
| CRTO | 0.200 g | 400.00 g |
| Kolliphor EL (Polyethoxylated castor oil) | 0.4542 g | 908.4 g |

TABLE 15-continued

Composition of curcuma drops of Example 6.

| Ingredients | Each ml contains | Qty. for 2 litres |
|---|---|---|
| Sucralose | 0.5 mg | 1 g |
| Flavouring agents | Q.S** | Q.S** |

**"Q.S" means quantity sufficient for the desired purpose, such as flavoring in the case of a flavoring agent.

The composition in Example 6 was prepared according to following process: Curcumin, CRTO, Kolliphor EL and ethanol were weighted and mixed to form a blend; the obtained blend was sonicated using Hiescher Ultra-sound sonicator for ten seconds at a time and resting for thirty seconds alternatively till a total power of 50,000 watts energy was reached to obtain curcumin solution. The curcumin solution was diluted in water by adding 1 to 10 ml of the solution to 200 ml of water to obtain a clear solution. The clear solution contains 1 mg/ml curcumin. Five drops (equivalent to 5 mg) can be placed under the tongue/buccal cavity.

Example 7

The composition of curcuma powder of Example 7 is shown in Table 16.

TABLE 16

Composition of curcuma powder of Example 7.

| Ingredients | Each ml contains | Qty. for 2 litres |
|---|---|---|
| Curcumin (95%) | 52.63 mg | 105.26 g |
| CRTO | 0.100 g | 200.00 g |
| Kolliphor EL (Polyethoxylated castor oil) | 0.4542 g | 908.40 g |
| PEG 6000 | 0.4248 g | 849.60 g |
| Sucralose | 0.5 mg | 1.0 g |
| Flavouring agent | Q.S. | Q.S. |

The composition in Example 7 was prepared according to following process: Curcumin, CRTO and Kolliphor EL were weighted and mixed to form a blend. The blend was sonicated using HiescherUltra-sound sonicator for ten seconds at a time and resting for thirty seconds alternatively till a total power of 50,000 watts energy was reached to obtain a thick paste. To the thick paste, PEG 6000 (melted at 60° C.) was added under continuous stirring to obtain a uniform mixture. The mixture was cooled to obtain a dry brittle mass which was pulverized to obtain curcuma powder.

Example 8

The composition of an orally soluble curcuma powder is shown in Table 17.

TABLE 17

Composition of an orally soluble curcuma powder of Example 8.

| Ingredients | Each ml contains | Qty. for 2 litres |
|---|---|---|
| Curcumin (95%) | 52.63 mg | 105.26 g |
| CRTO | 0.100 g | 200.00 g |
| Kolliphor EL (Polyethoxylated castor oil) | 0.4542 g | 908.40 g |

TABLE 17-continued

Composition of an orally soluble curcuma powder of Example 8.

| Ingredients | Each ml contains | Qty. for 2 litres |
|---|---|---|
| Maltodextrin | 0.4248 g | 849.60 g |
| Sucralose | 0.5 mg | 1.00 g |
| Flavouring agent | Q.S. | Q.S. |

The composition in Example 8 was prepared according to Example 7, other than PEG 6000 is replaced with maltodextrin.

Example 9 The composition of an orally soluble curcuma tablets is shown in Table 18.

TABLE 18

Composition of an orally soluble curcuma tablet of Example 9.

| Ingredients | Each ml contains | Qty. for 2 litres |
|---|---|---|
| Curcumin (95%) | 52.63 mg | 105.26 g |
| CRTO | 0.100 g | 200.00 g |
| Kolliphor EL (Polyethoxylated castor oil) | 0.4542 g | 908.40 g |
| PEG 6000 | 0.4248 g | 849.60 g |
| Sucralose | 0.5 mg | 1.00 g |
| Mannitol/Sorbitol | Q.S. | Q.S. |
| Flavouring agent | Q.S. | Q.S. |

The composition in Example 9 was prepared according to following process: Initially curcuma powder was formed according to the Example 7. Suitable excipients were then added to the curcuma powder to form tablets.

Example 10

The composition of an orally soluble curcuma tablets is shown in Table 19.

TABLE 19

Composition of an orally soluble curcuma tablet of Example 10.

| Ingredients | Each ml contains | Qty. for 2 litres |
|---|---|---|
| Curcumin (95%) | 52.63 mg | 105.26 g |
| CRTO | 0.100 g | 200.00 g |
| Kolliphor EL (Polyethoxylated castor oil) | 0.4542 g | 908.40 g |
| Maltodextrin | 0.4248 g | 849.60 g |
| Sucralose | 0.5 mg | 1.00 g |
| Mannitol/Sorbitol | Q.S. | Q.S. |
| Flavouring agent | Q.S. | Q.S. |

The composition in Example 10 was prepared according to Example 09, other than PEG 6000 is replaced with maltodextrin.

Example 11

The composition of an orally soluble curcuma lozenges is shown in Table 20.

TABLE 20

Composition of an orally soluble curcuma lozenges of Example 11.

| Ingredients | Each ml contains | Qty. for 2 litres |
|---|---|---|
| Curcumin (95%) | 52.63 mg | 105.26 g |
| CRTO | 0.100 g | 200.00 g |

TABLE 20-continued

Composition of an orally soluble curcuma lozenges of Example 11.

| Ingredients | Each ml contains | Qty. for 2 litres |
|---|---|---|
| Kolliphor EL (Polyethoxylated castor oil) | 0.4542 g | 908.40 g |
| PEG 6000 | 0.4248 g | 849.60 g |
| Sucralose | 0.5 mg | 1.00 g |
| Sorbitol | Q.S. | Q.S. |
| Flavouring agent | Q.S. | Q.S. |

The composition in Example 11 was prepared according to following process: Initially curcuma powder was formed according to the Example 7. Suitable excipients were then added to the curcuma powder to form lozenges.

Example 12

The composition of curcuma lozenges is shown in Table 21.

TABLE 21

Composition of an orally soluble curcuma tablet of Example 12

| Ingredients | Each ml contains | Qty. for 2 litres |
|---|---|---|
| Curcumin (95%) | 52.63 mg | 105.26 g |
| CRTO | 0.100 g | 200.00 g |
| Kolliphor EL (Polyethoxylated castor oil) | 0.4542 g | 908.40 g |
| Maltodextrin | 0.4248 g | 849.60 g |
| Sucralose | 0.5 mg | 1.00 g |
| Sorbitol | Q.S. | Q.S. |
| Flavouring agent | Q.S. | Q.S. |

The composition in Example 12 was prepared according to Example 11, other than PEG 6000 is replaced with maltodextrin.

Example 13

The composition of curcuma loaded transdermal patches is shown in Table 22.

TABLE 22

Composition of curcuma loaded transdermal patches of Example 13.

| Ingredients | Each gm contains |
|---|---|
| Curcumin (95%) | 52.63 mg |
| CRTO | 0.100 g |
| Kolliphor EL (Polyethoxylated castor oil) | 0.4542 g |
| HPMC-50 cps | 400.00 mg |
| Ethyl cellulose | 800.00 mg |
| Ethanol | 12.00 ml |
| Methylene Chloride | 8.00 ml |
| Diethyl phthalate | 0.20 ml |

The composition in Example 13 was prepared according to following process: The composition in Example 13 was prepared according to following process: curcumin, CRTO and Kolliphor EL were mixed to form a curcuma mixture, the mixture in the vessel was sonicated using Hiescher Ultra-sound sonicator for ten seconds at a time and resting for thirty seconds alternatively till a total power of 50,000 watts energy was reached to obtain a curcuma paste. A solvent mixture was prepared by mixing ethanol and methylene chloride. A polymer mixture was formed by mixing HPMC and ethyl cellulose. The solvent mixture and polymer mixture were mixed together to obtain a polymer solution. Diethyl phthalate and the curcuma paste was mixed to the polymer solution to form a uniform blend. The uniform blend was poured on Petri plate and dried to obtain a film.

Example 14

The composition water-soluble curcuma powder is shown in Table 23.

TABLE 23

Composition of water-soluble curcuma powder of Example 14.

| Ingredients | Each gm contains |
|---|---|
| CURCUMIN (95%) | 52.63 mg |
| TO | 0.100 g |
| CAPTEX 300 (Medium Chain triglyceride) | 0.100 mg |
| KOLLIPHOR EL | 0.4542 g |
| PEG 6000 | 0.4248 g |
| SUCRALOSE^ | 0.50 gm |

Note:
"A" means Sucralose may be replaced with other sweetening agents.

The composition in Example 14 was prepared by following process: curcumin, Captex 300 and Kolliphor EL were mixed to form a mixture, the mixture in the vessel was sonicated using Hiescher Ultra-sound sonicator for ten seconds at a time and resting for thirty seconds alternatively till a total power of 50,000 watts energy was reached to obtain curcuma paste; the curcuma paste was mixed with PEG-6000 melted at 60° C. and poured on a butter paper lined stainless steel tray and allowed to cool at room temperature to obtain a dry brittle mass; the dry brittle mass was pulverized and passed through #40 mesh sieve to obtain water soluble curcuma powder. Pharmaceutically acceptable diluents or fillers or binders and sweeteners and flavouring agents are added to the curcuma powder.

Example 15

The composition of orally soluble curcuma tablet is shown in Table 24.

TABLE 24

Composition of orally soluble curcuma tablet of Example 15.

| Ingredients | Each gm contains |
|---|---|
| CURCUMIN (95%) | 52.63 mg |
| TO | 0.100 g |
| CAPTEX 300 (Medium Chain triglyceride) | 0.100 mg |
| KOLLIPHOR EL | 0.4542 g |
| PEG 6000 | 0.4248 g |
| Sucralose*** | 0.50 mg |
| Mannitol/Sorbitol | Q.S** |
| Flavouring agents | Q.S** |

Curcuma powder was obtained according to process described in Example 14. Then pharmaceutically acceptable excipients were added, mixed and blended to the curcuma powder to obtain a mixture. The mixture was compressed to produce conventional tablets and orally soluble tablets.

Example 16

The composition of curcuma lozenges is shown in Table 25.

TABLE 25

Composition of curcuma lozenges of Example 16.

| Ingredients | Each gm contains |
|---|---|
| CURCUMIN (95%) | 52.63 mg |
| TO | 0.100 g |
| CAPTEX 300<br>Medium Chain triglyceride | 0.100 mg |
| KOLLIPHOR EL<br>(Polyethoxylated castor oil) | 0.4542 g |
| PEG 6000 | 0.4248 g |
| Sucralose | 0.50 mg |
| Sorbitol | Q.S** |
| Flavours | Q.S** |

Curcuma powder was obtained according to process described in Example 14. Then pharmaceutically acceptable excipients were added, mixed and blended to the curcuma powder to obtain a mixture. The mixture was compressed to produce conventional lozenges and orally soluble lozenges. Sorbitol may be replaced by hard boiled candy/confectionary's sugar/Mannitol etc.

Example 17

The composition of curcuma nanodrops is shown in Table 26.

TABLE 26

Composition of water-soluble curcuma drops of Example 17.

| Ingredients | Each ml contains |
|---|---|
| CURCUMIN (95%) | 52.63 mg |
| ETHANOL | 0.4248 g |
| TO | 0.100 g |

TABLE 26-continued

Composition of water-soluble curcuma drops of Example 17.

| Ingredients | Each ml contains |
|---|---|
| CAPTEX 300<br>Medium Chain triglyceride | 0.100 mg |
| KOLLIPHOR EL | 0.4542 g |
| Hydroxy Propyl Methyl Cellulose | 0.23 mg |
| Propylene Glycol | 0.05 g |
| Sucralose | 0.50 g |

The composition in Example 17 was prepared according to following process: curcumin, TO, Captex 300, Kolliphor EL and ethanol were weighted and mixed to form a blend; the obtained blend was sonicated using Hiescher Ultrasound sonicator for ten seconds at a time and resting for thirty seconds alternatively till a total power of 50,000 watts energy was reached to obtain curcuma solution.

Methods for Physical, Chemical and Functional Analysis of Curcuma Formulations

Particle Size Analysis

The particle size of raw materials (curcumin powder, CRTO, TO) and formulated products (examples 1, 2, 3 and 4) were determined using Brookhaven particle analyzer (BPA) using zeta potential principle. BPA works on the principle that when a beam of light (a laser) is scattered by a group of particles, the angle of light scattering is inversely proportional to particle size (i.e. the smaller the particle size, the larger the angle of light scattering). The Nano particle analyser utilizes backscattering to measure measures using backscattering the size of the particles by building the correlation function. Brookhaven's' Nano instrument is the go-to-solution for characterization of nanoparticles, macromolecular assemblies and other molecules/particles of small sizes. The raw material (CRTO/TO/curcumin powder) has different bigger particle size. After formulation and subjecting to nanonization process, the starting material size in the average range of 2 μm is changed to 40-157 nm. Table 27 depicts physical parameters such as (effective diameter and polydispersity) of raw materials and finished products as measured by Brookhaven instruments.

TABLE 27

The physical parameters of raw materials and finished products.

| | Curcumin Powder | CRTO | TO | Example 1 | Example 2 | Example 3 | Example 4 |
|---|---|---|---|---|---|---|---|
| Effective Diameter | 2743.2 nm | 441.2 nm | 1033.1 mm | 46.0 nm | 59.7 nm | 53.8 nm | 157.0 nm |
| Polydispersity | 0.380 | 0.005 | 0.331 | 0.312 | 0.312 | 0.321 | 0.265 |

FIG. 3 represents the correlation between the particle size and time taken for shift (Shift time or lag time). The smaller the particle size, the less the time taken for the sample. From the graphical representation of FIG. 3*a* to FIG. 3*g*, it can be inferred that as the particle size of the raw material is nanonized, the nanonized formulations showed less time lag. The size distribution of raw materials and formulated samples are graphically represented on FIG. 4*a* to FIG. 4*g*. The FIG. 4 represents that as the size of the particle increases, the intensity increases proportionally upto median diameter after which the diameter of the particle has no significant effect and the intensity consistently decreases. However, the stability of the particle increases with further increase in size and eventually attains a plateau.

Zeta Potential Study

The zeta potential of the four formulations are depicted in Table 28. The zeta potential (also known as electrokinetic potential) is established on the surface of any material when it comes in contact with a liquid medium. The zeta potential of particles is a key indicator of the stability of a colloidal dispersion, since it reflects the ability of particles to repulse each other electrostatically. The emulsions with high zeta potential are electrically stabilized due to continuous Brownian movement whereas the emulsion with no or very less zeta potential tend to agglomerate leading to poor stability. The high negative zeta potential of all examples 01 to 04 depicts that the curcuma formulation is stable as emulsion for long duration, wherein the long duration is at-least 6 months.

TABLE 28

The zeta potential values of the four formulations (Samples of Examples 1, 2, 3 and 4)

| S.No. | Name of the product | Zeta Potential | Conclusion |
|---|---|---|---|
| 1 | Example 1 | −15.03 mV | The zeta potential value indicates that the colloidal system is stable. |
| 2 | Example 2 | −14.23 mV | The zeta potential value indicates that the colloidal system is stable. |
| 3 | Example 3 | −13.26 mV | The zeta potential value indicates that the colloidal system is stable. |
| 4 | Example 4 | −11.90 mV | The zeta potential value indicates that the colloidal system is stable. |

Stability Study

The stability study of curcuma liquid drops was performed by storing curcuma liquid drop samples at temperatures 25° C.±2° C. with relative humidity 60%±5% and at temperature 40° C.±2° C. with relative humidity 75%±5%. It was observed that curcuma liquid drop samples showed good stability upto 12 months based on the available stability data as shown in Table 29. Different molar ratio of the formulated Example 1 (an ethanol formulation) and Example 2 (a PG formulation) were tested under above mentioned varied temperature and relative humidity.

TABLE 29

Parameters for stability study for Example 1 and Example 2 at two different temperature and relative humidity

| | | 40° C. ± 2° C./75% ± 5% RH[#] | | | | 25° C. ± 2° C./60% ± 5% RH | | | |
|---|---|---|---|---|---|---|---|---|---|
| | Initial | 1M | 2M | 3M | 6M | 3M | 6M | 9M | 12M |
| Example 1 | | | | | | | | | |
| Assay | 100.1 | 99.1 | 98.2 | 101.3 | 98.8 | 101.9 | 100.8 | 99.7 | 98.5 |
| PH | 7.48 | 7.25 | 7.22 | 7.16 | 7.25 | 7.48 | 7.41 | 7.38 | 7.45 |
| wt/ml | 0.9434 | 0.9337 | 0.9546 | 0.9417 | 0.9402 | 0.9427 | 0.9308 | 0.9507 | 0.9301 |
| Example 2 | | | | | | | | | |
| Assay | 98.5 | 97.9 | 98.1 | 97.3 | 96.9 | 98.2 | 98.0 | 97.9 | 97.5 |
| PH | 7.28 | 7.15 | 7.24 | 7.23 | 7.19 | 7.18 | 7.11 | 7.18 | 7.25 |
| wt/ml | 0.9632 | 0.9648 | 0.9589 | 0.9589 | 0.9500 | 0.9647 | 0.9628 | 0.9647 | 0.9612 |

[#]RH: Relative humidity

Figure 2:
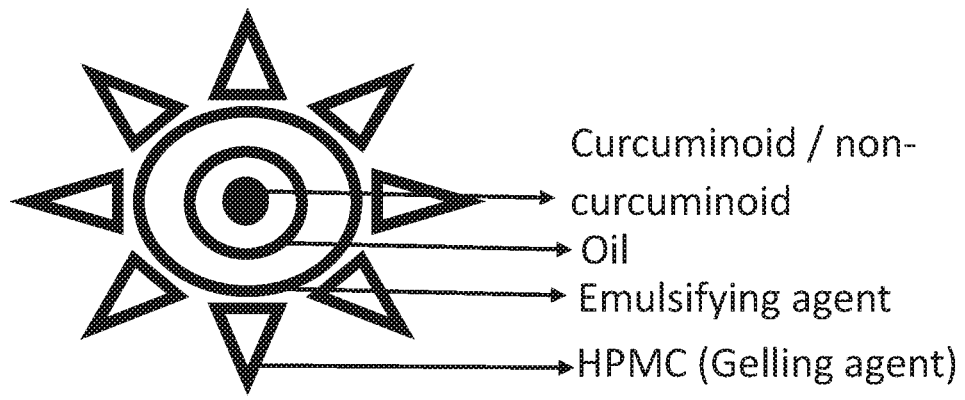
FIG. 2 shows schematic representation of Curcuma composite particles.
Figure 3A:
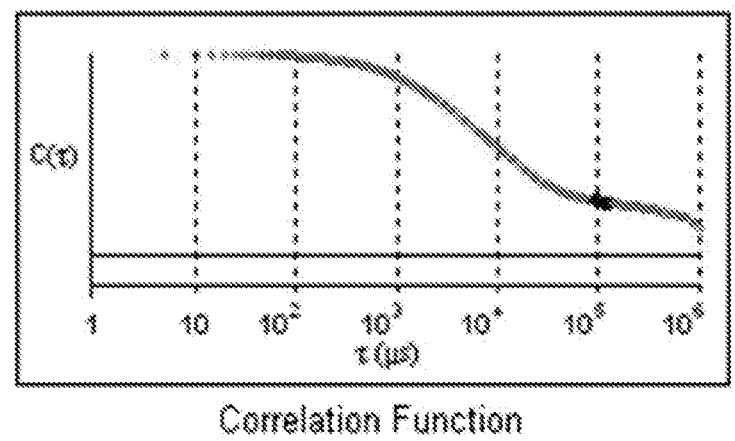
FIG. 3a shows graphical correlation between the particle size and time taken for shift (Shift time or lag time) of curcumin powder.
Figure 3B:
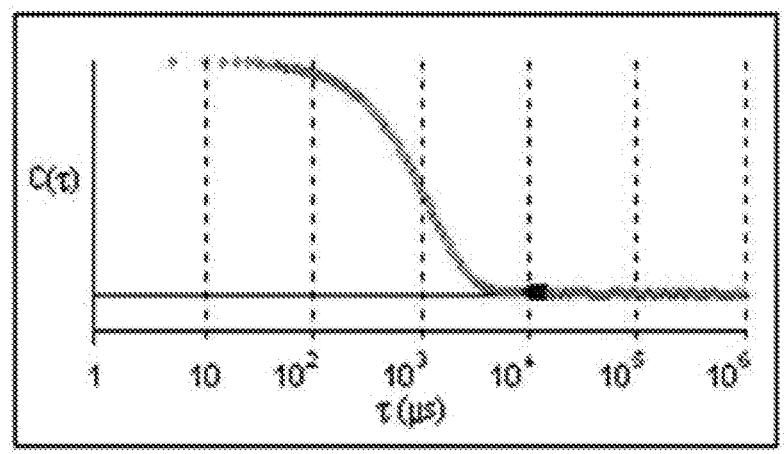
FIG. 3b shows graphical correlation between the particle size and time taken for shift (Shift time or lag time) of CRTO.
Figure 3C:
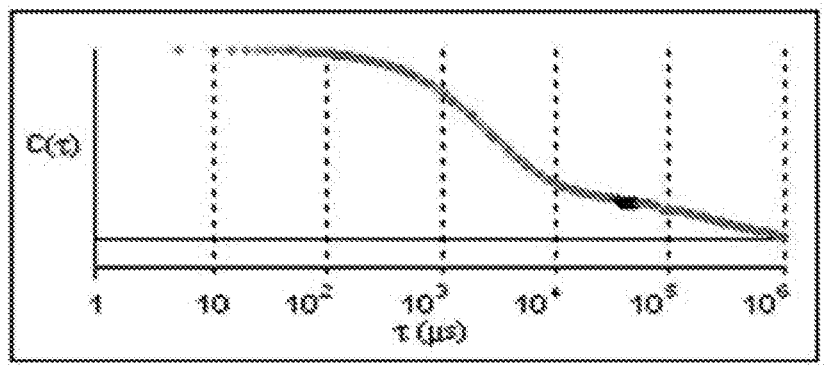
Figure 3D:
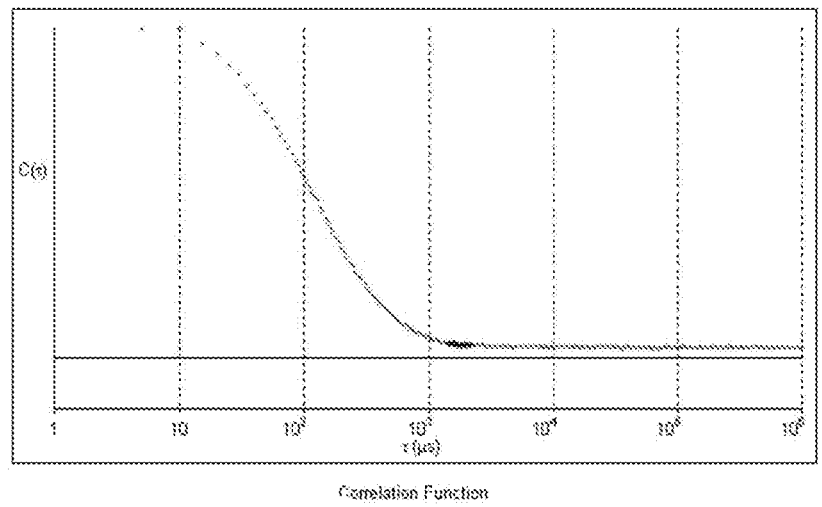
FIG. 3d shows graphical correlation between the particle size and time taken for shift (Shift time or lag time) of Example 1.
Figure 3E:
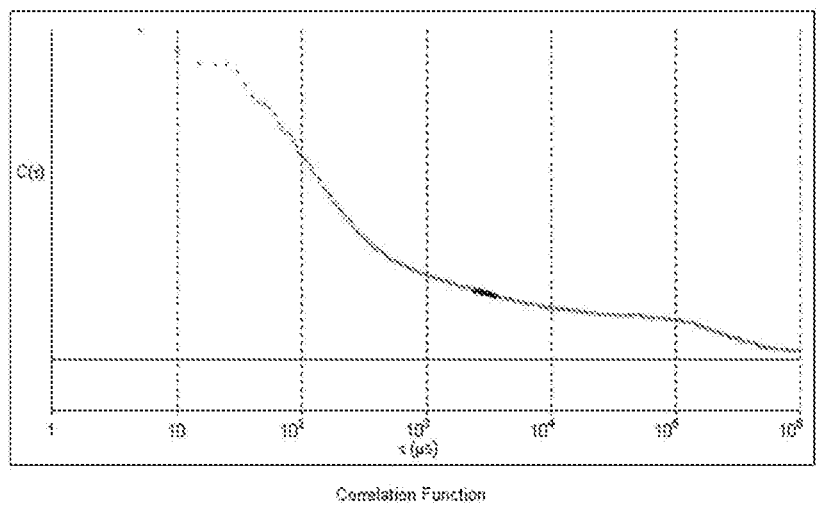
FIG. 3e shows graphical correlation between the particle size and time taken for shift (Shift time or lag time) of Example 2.
Figure 3F:
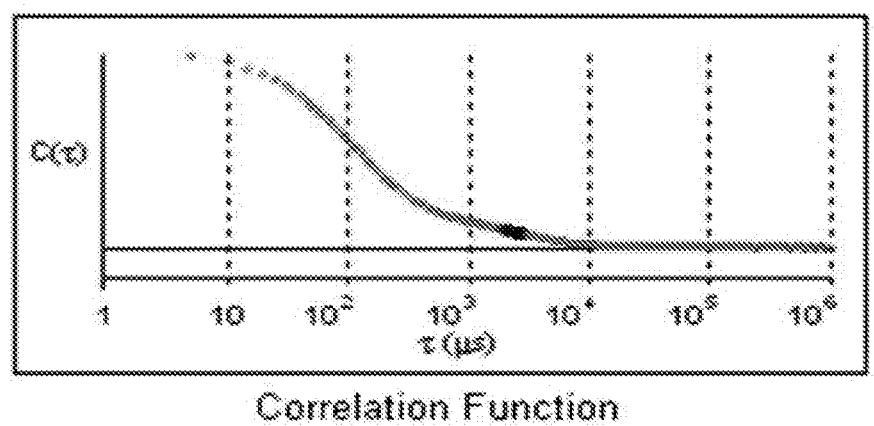
FIG. 3f shows graphical correlation between the particle size and time taken for shift (Shift time or lag time) of Example 3.
Figure 3G:
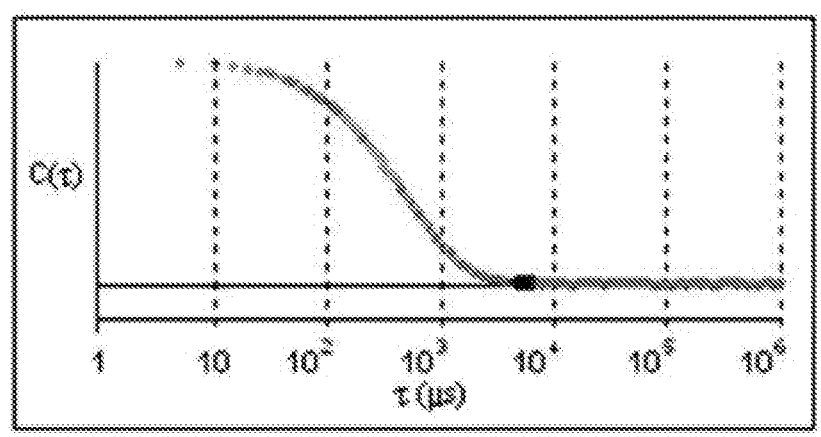
FIG. 3g shows graphical correlation between the particle size and time taken for shift (Shift time or lag time) of Example 4.
Figure 4A:
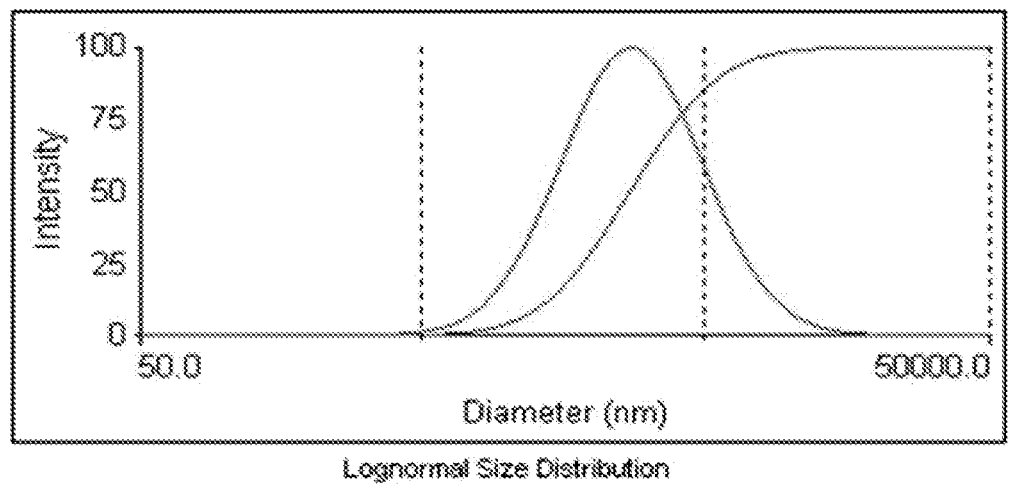
FIG. 4a shows particle size distribution of curcumin powder.
Figure 4B:
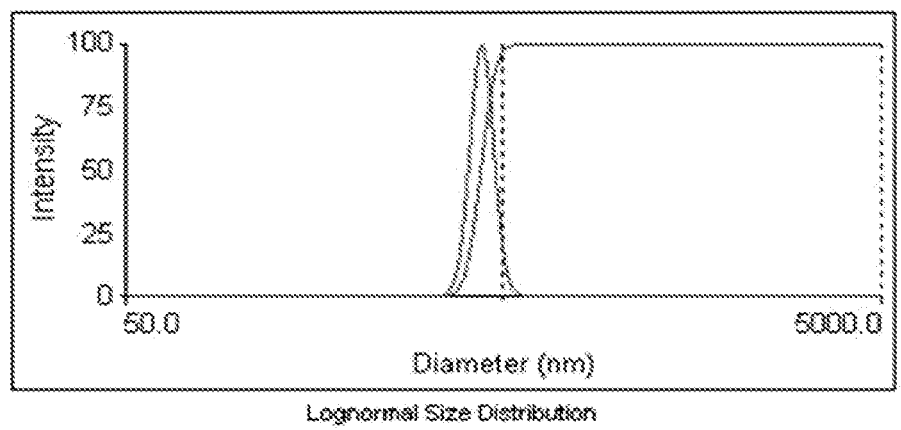
FIG. 4b shows particle size distribution of CRTO.
Figure 4C:
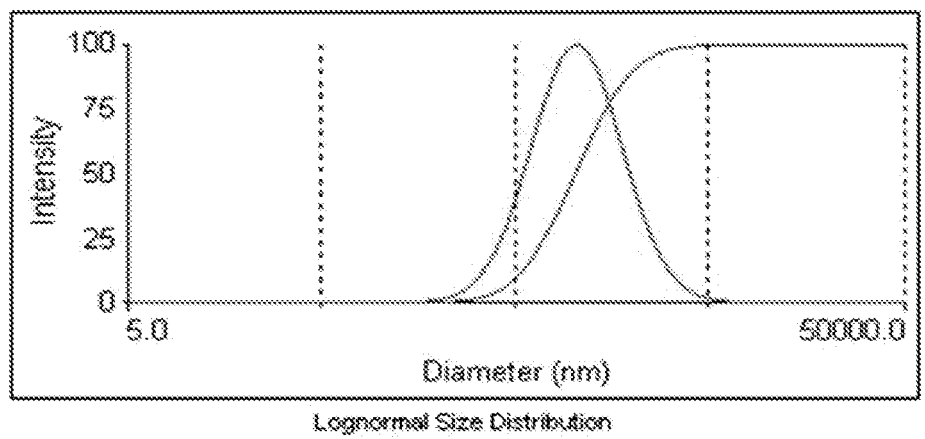
Figure 4D:
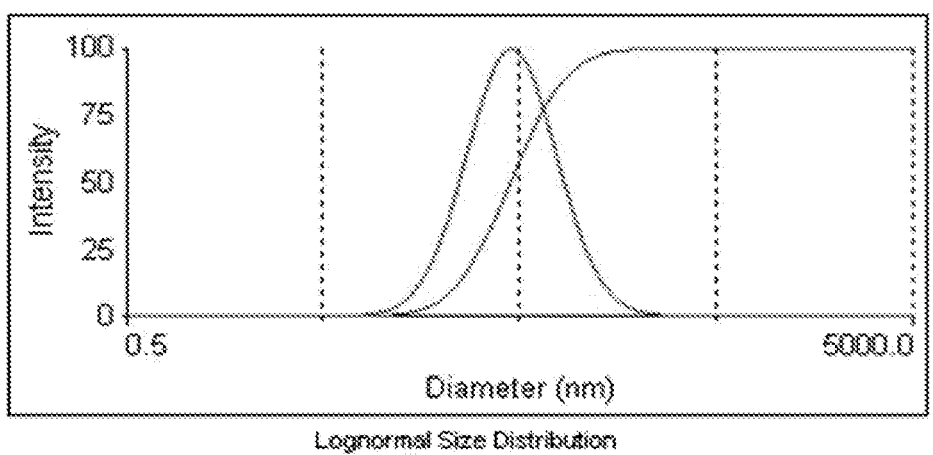
FIG. 4d shows particle size distribution of Example 1.
Figure 4E:
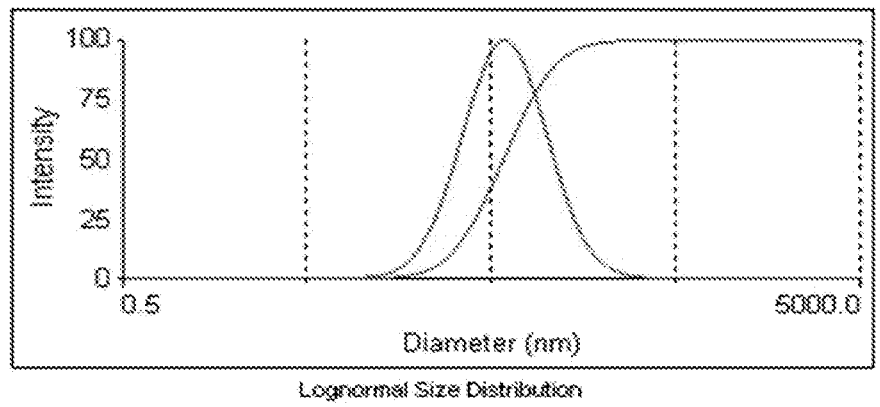
FIG. 4e shows particle size distribution of Example 2.
Figure 4F:
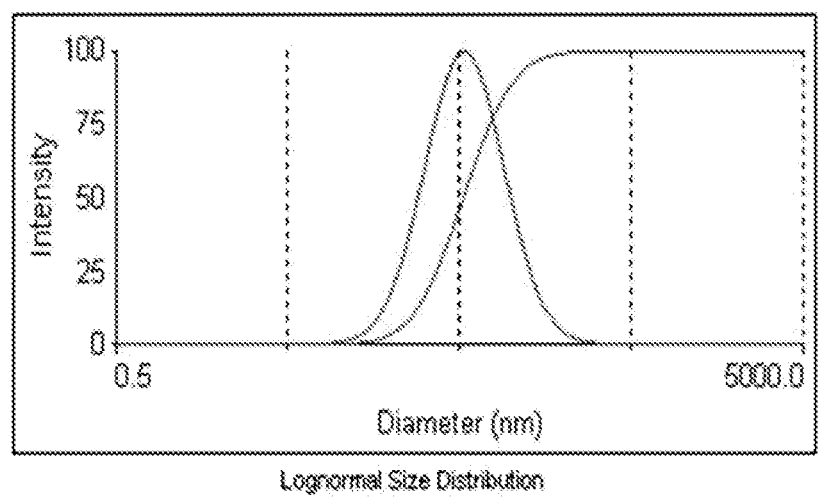
FIG. 4f shows particle size distribution of Example 3.
Figure 4G:
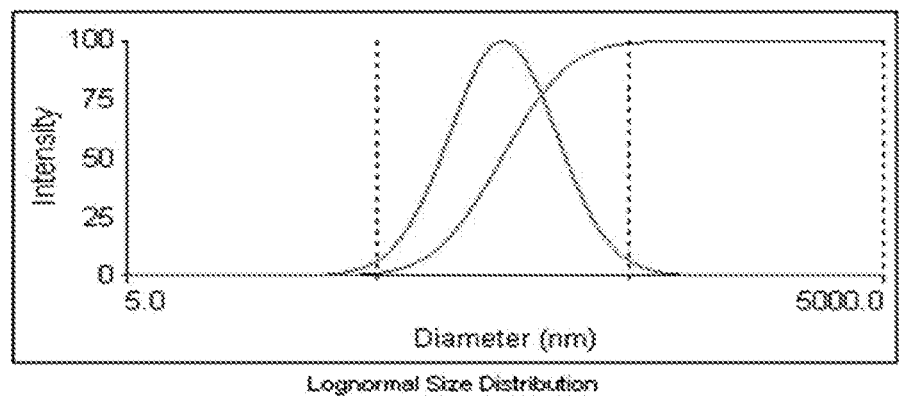
FIG. 4g shows particle size distribution of Example 4.
Figure 5A:
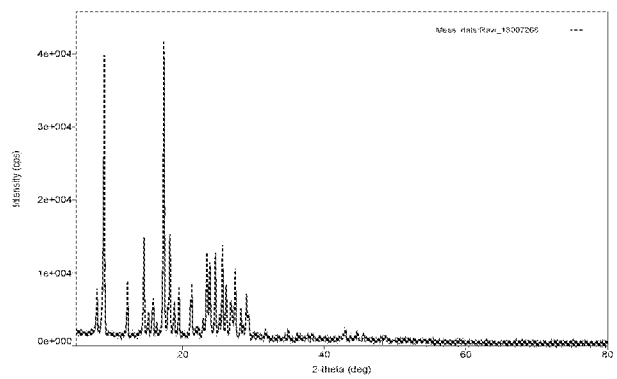
FIG. 5a shows XRD of curcumin powder.
Figure 5B:
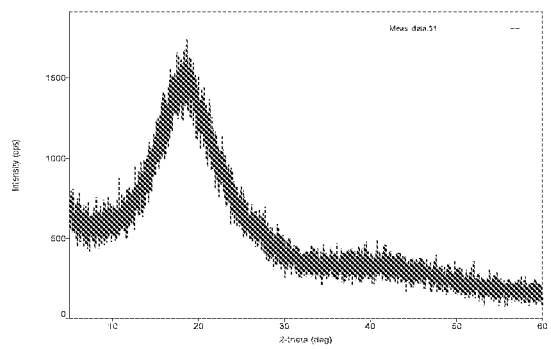
FIG. 5b shows XRD of CRTO.
Figure 5C:
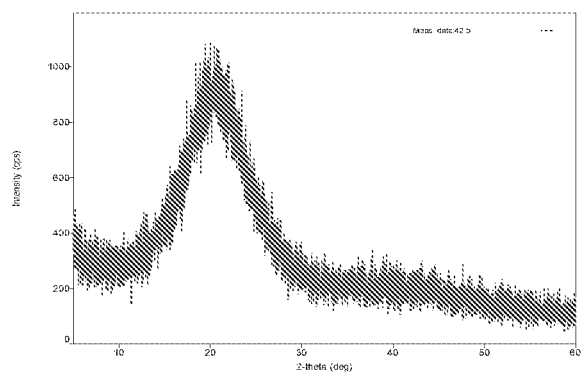
FIG. 5c shows XRD of Curcuma Drops (Curcumin+CRTO) Formulation in PEG base.
Figure 5D:
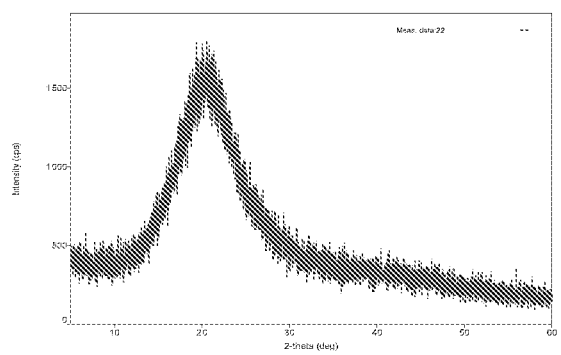
FIG. 5d shows XRD of Curcuma Drops (Curcumin+CRTO) Formulation in PG base.
Figure 5E:
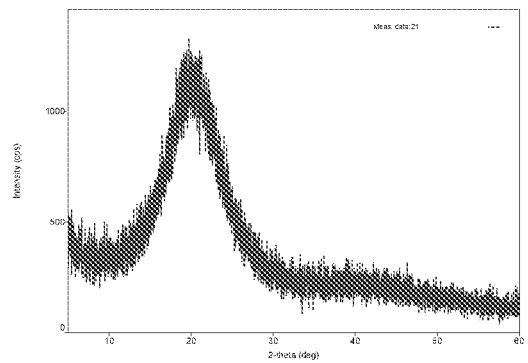
FIG. 5e shows XRD of Curcuma Drops (Curcumin+CRTO) Formulation in Ethanol base.
Figure 5F:
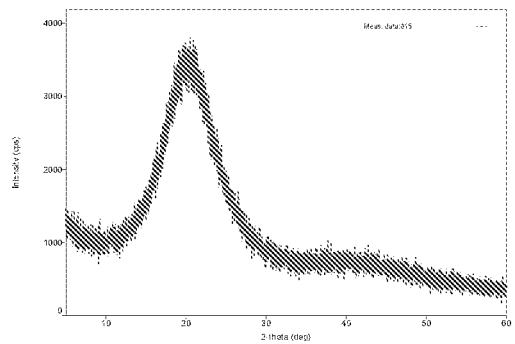
FIG. 5f shows XRD of Curcuma Drops (Curcumin+CRTO) Formulation in Ethanol base.
Figure 5G:
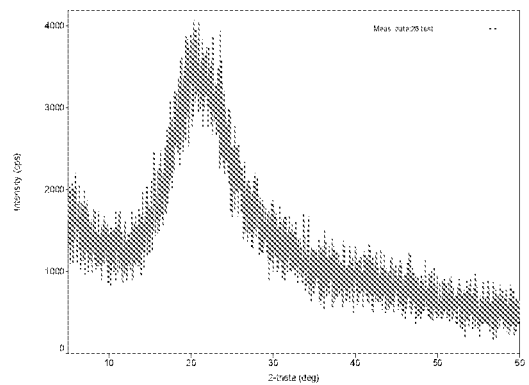
FIG. 5g shows XRD of Curcuma Drops (Curcumin+CRTO) Formulation in PEG base.
Figure 6E:
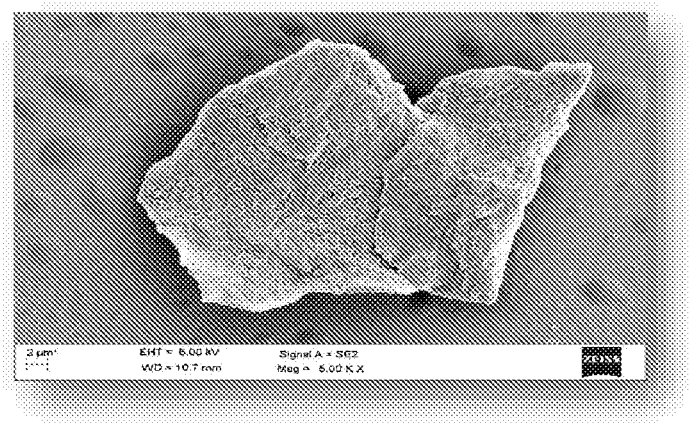
FIG. 6e shows SEM image of finished product as curcuma liquid drops.
Figure 6E:
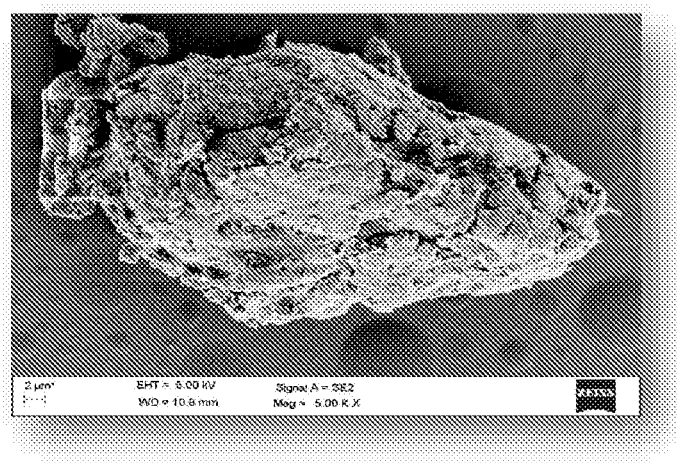

Structural and Topographical Study:

The structural evidence of raw material and formulated products were determined by X-ray diffraction (XRD) and scanning electron microscopy (SEM). XRD is used to identify the crystalline phases present in a material and thereby reveal chemical composition information. Each globule comprises the active constitute in a very uniform disperse manner. The graphical representation received from XRD is shown in FIG. 5. The FIG. 5a represents the pattern for curcumin powder which is crystalline in nature, FIG. 5b proves the amorphous structure of CRTO. The XRD of curcuma drops formulation prepared in polyethylene glycol (PEG) and propylene glycol (PG) using curcumin powder and CRTO as raw materials and excipients are depicted in FIGS. 5c and 5d respectively. The XRD of curcuma drops formulation prepared in ethanol using curcumin powder and CRTO as raw materials and excipients are depicted in FIG. 5d and FIG. 5e. FIG. 5f also depicts the curcuma drops formulation prepared in polyethylene glycol (PEG base) using curcumin powder and CRTO as raw materials and excipients. The XRD graph proves the amorphous structure of formulation, which was achieved after mixing curcumin with suitable excipients and nanonization process (particle size reduction). The XRD study of raw material and finished product shows that crystalline form of raw material through blending and homogenization slowly converts into amorphous form. The amorphous form aid in solubilizing the product and remain stable for long duration. SEM give information on surface topography and composition. SEM pictures of raw material curcumin powder are depicted in FIG. 6a (1) and FIG. 6a (2). The figures show big cubical blocks structure of curcumin powder. The FIG. 6a (2) is twice more magnified than FIG. 6a (1). FIG. 6b is SEM image of CRTO. During formulation process curcumin powder and CRTO along with excipients are blended, homogenized and sonicated to give the finished product. FIG. 6c (1) and FIG. 6c (2) depict in-process blended structure. FIG. 6c (2) is 5 times more magnified than FIG. 6c (1). FIG. 6d (1), 6d (2), 6d (3) and 6d (4) depicts SEM view of varied topographical region in the intermediate steps of homogenization step. The FIG. 6e depicts the SEM image of the finished product. The SEM images at varied formulation stages depicts that raw materials are nanonized and is appropriately coated with excipients. The SEM analysis substantiates the schematic depiction of a curcuminoid or a non-curcuminoid particle in FIG. 2 wherein the process of the particles of a curcuminoid or a non-curcuminoid being coated with the excipients along with sonication results in enhanced solubility of the particles in the formulation as well as when the formulation is diluted in aqueous medium.

PUBLICATIONS INCORPORATED BY REFERENCE

All publications and references, including patents and publications, cited herein the application are incorporated by reference in their entirety.

Nagarajan, S., Kubra, I. R., & Rao, L. J. M. (2010). Separation of curcuminoids enriched fraction from spent turmeric oleoresin and its antioxidant potential. *Journal of food science*, 75(6), H158-H162.

Ravindranath, V., Chandrasekhara, N., 1980. Absorption and tissue distribution of curcumin in rats. Toxicology 16, 259-265.

Preetha Anand, Ajaikumar B. Kunnumakkara, Robert A. Newman, and Bharat B. Aggarwal Molecular Pharmaceutics 2007 4 (6), 807-818

Gera, M., Sharma, N., Ghosh, M., Huynh, D. L., Lee, S. J., Min, T., ... & Jeong, D. K. (2017). Nano compositions of curcumin: an emerging paradigm for improved remedial application. *Oncotarget*, 8(39), 66680.

Subramani, P. A., Panati, K., Lebaka, V. R., Reddy, D. D., & Narala, V. R. (2017). Nanostructures for Curcumin Delivery: Possibilities and Challenges. In *Nano-and Microscale Drug Delivery Systems* (pp. 393-418). Elsevier.

Jayaprakasha, G. K., Negi, P. S., Anandharamakrishnan, C., & Sakariah, K. K. (2001). Chemical composition of turmeric oil-A by product from turmeric oleoresin industry and its inhibitory activity against different fungi. *Zeitschrift für Naturforschung C*, 56(1-2), 40-44.

Ferreira, C. M., Pinto, I. S., Soares, E. V., & Soares, H. M. (2015). (Un) suitability of the use of pH buffers in biological, biochemical and environmental studies and their interaction with metal ions—a review. *RSC Advances*, 5(39), 30989-31003.

Bagchi, A. (2012). Extraction of curcumin. IOSR Journal of Environmental Science, Toxicology and Food Technology, 1(3), 1-16.

Anand, P., Kunnumakkara, A. B., Newman, R. A., & Aggarwal, B. B. (2007). Bioavailability of curcumin: problems and promises. Molecular pharmaceutics, 4(6), 807-818.

Khedekar and Mittal, (2013) SELF EMULSIFYING DRUG DELIVERY SYSTEM: A REVIEW, International Journal of Pharmaceutical Sciences and Research Vol. 4(12): 4494-4507; Vol. 4(12): 4494-4507

Wadhwa, J., Nair, A., & Kumria, R. (2012). Emulsion forming drug delivery system for lipophilic drugs. *Acta Pol Pharm*, 69(2), 179-91.

Exbrayat, J. M., Moudilou, E. N., & Lapied, E. (2015). Harmful effects of nanoparticles on animals. Journal of Nanotechnology, 2015.

Nair, A., Amalraj, A., Jacob, J., Kunnumakkara, A. B., & Gopi, S. (2019). Non-Curcuminoids from Turmeric and Their Potential in Cancer Therapy and Anticancer Drug Delivery Formulations. Biomolecules, 9(1), 13.

What is claimed is:

1. A formulation comprising a particle having
   a) a turmeric oleoresin or a curcumin removed turmeric oleoresin in an amount 5 w/w % to 70 w/w %,
   b) a non-ionic oil in water emulsifier in an amount 30 w/w % to 45 w/w %,
   c) a curcuminoid in an amount of 1% to 10% w/w %,
   wherein the formulation is water soluble and therapeutically safe, wherein the formulation does not contain a pH buffer, natural emulsifier, or turmeric essential oil and the particle has an average particle size in a range of 40 nm to 1000 nm.

2. The formulation of claim 1, wherein the formulation comprises about 40 to 70 weight % of the turmeric oleoresin, wherein the turmeric oleoresin comprises of about 50 to 97 weight % of the curcuminoid and 50-99 weight % of a turmerone.

3. The formulation of claim 1, wherein the non-ionic oil-in-water emulsifier is selected from polyoxyethylene products of a hydrogenated vegetable oil, a polyethoxylated castor oil, a polyethoxylated hydrogenated castor oil, a polyoxyethylene-sorbitan-fatty acid ester, a polyoxyethylene castor oil derivative and/or a combination thereof.

4. The formulation of claim 1, further comprising a solvent, wherein the solvent comprises ethyl alcohol, isopropyl alcohol, glycofurol, a polyethylene glycol, glycerol, a polypropylene glycol, a propylene glycol, N-methyl-2-pyrolidone or mixture thereof.

5. The formulation of claim 1, further comprising a lipophilic solvent comprises a triglyceride.

6. The formulation of claim 5, wherein the triglyceride comprises a caprylic triglyceride, a chain fatty acid triglyceride containing oil, propylene glycol dicaprylate.

7. The formulation of claim 1, further comprising an adsorbent, wherein the adsorbent comprises a polyethylene glycol, a maltodextrin, a soluble starch, a hydrolysed starch, a fiber, a water soluble oligo saccharide, a chicory, a dextran, a cellulose, a copolymer of polyvinylpyrrolidone, a sugar alcohol, a sorbitol, a xylitol, a mannitol, a cellulose derivative or combinations thereof, wherein the cellulose derivative comprises a hydroxypropylmethyl cellulose, a hydroxypropyl cellulose, a cyclodextrine or combinations thereof.

8. The formulation of claim 1, further comprising a diluent, a filler or a binder, wherein the diluent, the filler or the binder comprises a mannitol, a sorbitol, a lactose, a candy, a sugar or combinations thereof.

9. The formulation of claim 1, further comprising a water-soluble polymer, wherein the water-soluble polymer comprises a polyglutamic acid, a polyethylene glycol, a propylene glycol, glycerol, a propylene glycol ester, a polyglycerol oleate polyvinyl alcohol, a non-ethoxylated polymer or combination thereof.

10. A method for producing the formulation of claim 1 comprising the steps of:
    a) mixing a curcuminoid, a curcumin removed turmeric oleoresin and a non-ionic emulsifier to form a blend;
    b) sonicating and resting the blend alternatingly to obtain a clear solution;
    c) preparing a water-soluble curcuma formulation, wherein the water-soluble curcuma formulation has properties as follows:
    1) solubilization of the curcuminoid in a turmeric oleoresin or the curcumin removed turmeric oleoresin or a turmeric oil or combination thereof using a lipophilic solvent, or non-ionic oil in water emulsifier or a solvent or a pharmaceutically acceptable excipient or combination thereof resulting in a clear solution having a percent sediment load of less than 30% or a soluble powder;
    2) addition of one or more additional pharmaceutically acceptable excipients to the clear solution obtained in step 1) comprising the curcuminoid, the turmeric oleoresin or the curcumin removed turmeric oleoresin or the turmeric oil or combination of the curcuminoid and the non-curcuminoid resulting in a clear solution having particles having an average number particle size in a range of 40 to 1000 nm;
    3) the formulation exhibits no precipitation or separation of the particles for a minimum period of 24 hours;
    4) the formulation exhibits no precipitation or separation of the particles for a minimum period of 15 minutes when added to water in a ratio of one part of the formulation in 200 parts of water.

* * * * *